(12) United States Patent
Xu et al.

(10) Patent No.: US 11,173,002 B2
(45) Date of Patent: Nov. 16, 2021

(54) FLEXIBLE SURGICAL INSTRUMENT SYSTEM

(71) Applicant: BEIJING SURGERII TECHNOLOGY CO., LTD., Beijing (CN)

(72) Inventors: Kai Xu, Beijing (CN); Zhengchen Dai, Beijing (CN); Shu'an Zhang, Beijing (CN); Jiangran Zhao, Beijing (CN); Zhixiong Yang, Beijing (CN); Huan Liu, Beijing (CN); Zhaoyu Zhang, Beijing (CN); Wei Wei, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 197 days.

(21) Appl. No.: 16/329,758

(22) PCT Filed: Aug. 31, 2017

(86) PCT No.: PCT/CN2017/099855
§ 371 (c)(1),
(2) Date: Feb. 28, 2019

(87) PCT Pub. No.: WO2018/041204
PCT Pub. Date: Mar. 8, 2018

(65) Prior Publication Data
US 2019/0239966 A1    Aug. 8, 2019

(30) Foreign Application Priority Data

Aug. 31, 2016  (CN) .......................... 201610796100.9
Aug. 31, 2016  (CN) .......................... 201610796118.9

(51) Int. Cl.
*A61B 34/30*  (2016.01)
*A61B 34/00*  (2016.01)
*A61B 17/00*  (2006.01)

(52) U.S. Cl.
CPC ............... *A61B 34/30* (2016.02); *A61B 34/70* (2016.02); *A61B 2017/00314* (2013.01);
(Continued)

(58) Field of Classification Search
CPC ........... A61B 34/30–37; A61B 2034/301–306; A61B 17/29–295;
(Continued)

(56) References Cited

U.S. PATENT DOCUMENTS

| 2011/0028991 | A1  | 2/2011  | Ikeda et al. |
| 2013/0090763 | A1* | 4/2013  | Simaan ............... A61B 5/11 700/258 |
| 2015/0352728 | A1* | 12/2015 | Wang ................. A61B 1/00 74/490.04 |

FOREIGN PATENT DOCUMENTS

| CN | 103315781 A | 9/2013 |
| CN | 103340707 A | 10/2013 |

(Continued)

OTHER PUBLICATIONS

ISA State Intellectual Property Office of the People's Republic of China, International Search Report Issued in Application No. PCT/CN2017/099855, dated Nov. 21, 2017, WIPO, 4 pages.
(Continued)

*Primary Examiner* — Erich G Herbermann
(74) *Attorney, Agent, or Firm* — McCoy Russell LLP

(57) ABSTRACT

Disclosed is a flexible surgical instrument system, comprising a flexible surgical instrument and a driving unit, wherein the flexible surgical instrument comprises a distal structural body, a proximal structural body and a middle connecting
(Continued)

body; the distal structural body comprises a distal structural segment, the distal structural segment comprising a distal spacing disk, a distal fixing disk and structural backbones; the proximal structural body comprises a proximal structural segment, the proximal structural segment comprising a proximal spacing disk, a proximal fixing disk and structural backbones; the middle connecting body comprises channel fixing and structural backbone guide channels; the driving unit comprises a motor part, a motion conversion part and linear motion mechanisms; the motor part comprises a first fixing plate and a first motor; the motion conversion part comprises transmission chains, the transmission chain converts a rotational output of the first motor into a linear motion of output rods, the linear motion is transferred to an input end of the linear motion mechanism through a sterile barrier, an output end of the linear motion mechanism is connected to one end of a driving backbone, the driving backbone passes through the proximal spacing disks, and the other end of the driving backbone is connected to the proximal fixing disk.

19 Claims, 20 Drawing Sheets

(52) U.S. Cl.
CPC ............... *A61B 2017/00323* (2013.01); *A61B 2017/00327* (2013.01); *A61B 2017/00398* (2013.01); *A61B 2017/00477* (2013.01); *A61B 2034/301* (2016.02); *A61B 2034/302* (2016.02); *A61B 2034/305* (2016.02)

(58) Field of Classification Search
CPC .......... A61B 2017/2901–2948; A61B 2017/00238–00362; A61B 34/71; A61B 17/00234; A61B 34/70; A61B 2017/00398; A61B 2017/00477; B25J 8/06; B25J 9/104
See application file for complete search history.

(56) References Cited

FOREIGN PATENT DOCUMENTS

| | | | |
|---|---|---|---|
| CN | 103340731 | A | 10/2013 |
| CN | 103707322 | A | 4/2014 |
| CN | 103948435 | A | 7/2014 |
| CN | 104758013 | A | 7/2015 |
| CN | 103707322 | B | 4/2016 |
| CN | 105751210 | A | 7/2016 |
| CN | 105792783 | A | 7/2016 |
| CN | 105856213 | A | 8/2016 |
| CN | 106308937 | A | 1/2017 |
| CN | 106361433 | A | 2/2017 |
| CN | 106377315 | A | 2/2017 |
| EP | 2008594 | A2 | 12/2008 |
| WO | 2009094670 | A1 | 7/2009 |
| WO | 2012015816 | A1 | 2/2012 |
| WO | 2014046618 | A1 | 3/2014 |
| WO | 2014046618 | A8 | 3/2014 |
| WO | 2015175200 | A1 | 11/2015 |
| WO | 2016081286 | A1 | 5/2016 |

OTHER PUBLICATIONS

State Intellectual Property Office of the People's Republic of China, First Search Issued in Application No. 201610796100.9, dated May 24, 2018, 4 pages.

State Intellectual Property Office of the People's Republic of China, First Search Issued in Application No. 201610796118.9, dated Jun. 18, 2018, 2 pages.

European Patent Office, Supplementary European Search Report Issued in Application No. 17845506.9, dated Mar. 25, 2020, Germany, 2 pages.

* cited by examiner

FLEXIBLE SURGICAL INSTRUMENT SYSTEM

CROSS REFERENCE TO RELATED APPLICATIONS

The present patent application is a U.S. national phase of Chinese International Application No. PCT/CN2017/099855 entitled "FLEXIBLE SURGICAL INSTRUMENT SYSTEM" and filed on Aug. 31, 2017. Chinese International Application No. PCT/CN2017/099855 claims priority to Chinese Patent Application No. 201610796100.9 filed on Aug. 31, 2016 and Chinese Patent Application No. 201610796118.9 filed on Aug. 31, 2016. The entire contents of each of the above-identified applications are incorporated herein by reference for all purposes.

TECHNICAL FIELD

The present invention relates to a flexible surgical instrument system with a distal end capable of turning in any direction, belonging to the field of medical instruments.

BACKGROUND ART

Multi-port laparoscopic minimally invasive surgery has occupied an important position in surgery because of its small incision and rapid postoperative recovery. The existing da Vinci surgical robot of the Intuitive Surgical, Inc. assists doctors in completing the multi-port laparoscopic minimally invasive surgery and has achieved great commercial success.

For the minimally invasive surgery, after the multi-port laparoscopic surgery, single-port laparoscopic surgery and natural orifice transluminal non-invasive surgery have been developed, which have less trauma to the patient and higher postoperative outcomes. However, in the single-port laparoscopic surgery and the natural orifice transluminal non-invasive surgery, all surgical instruments including a visual illumination module and a surgical operating arm have access to the surgical site through a single channel, which is extremely stringent for the preparation of the surgical instruments. A distal structure of the existing surgical instrument mainly consists of multiple rods hinged in series, and is driven by a pulling force from a steel wire rope, so that the surgical instrument can turn at a hinge joint. Since the steel wire rope has to be continuously tensioned by a pulley, this driving method has difficulty in further miniaturizing the surgical instrument, and also has difficulty in further improving the moving performance of the instrument.

Although the Intuitive Surgical, Inc. has recently introduced a da Vinci Single-Site surgical robot, in which the original rigid surgical instrument is modified into a semi-rigid surgical instrument and a pre-bent sleeve is additionally provided so as to improve the moving performance of the surgical instrument to a certain extent, it still cannot fundamentally solve the problems faced by the traditional microsurgical instruments.

SUMMARY OF THE INVENTION

In view of the above problems, an object of the present invention is to provide a flexible surgical instrument system with a distal end capable of turning in any direction, which can be better applied to a robot system that passes through a natural orifice of human body or a single surgical incision and performs an operation.

In order to achieve the above object, following technical solution is used in the invention: a flexible surgical instrument system comprising a flexible surgical instrument and a driving unit, wherein the flexible surgical instrument comprises a flexible continuous body structure composed of a distal structural body, a proximal structural body and a middle connecting body; the distal structural body comprises at least one distal structural segment comprising distal spacing disks, a distal fixing disk and structural backbones; the proximal structural body comprises a proximal structural segment comprising proximal spacing disks, a proximal fixing disk and structural backbones; the middle connecting body comprises two channel fixing plates and structural backbone guide channels provided between the two channel fixing plates; the structural backbones of the distal structural segment are securely connected, in one-to-one correspondence, to or are the same as the structural backbones of the proximal structural segment, one end of each of the structural backbones is securely connected to the proximal fixing disk, passing through the proximal spacing disks, the structural backbone guide channel, and the distal spacing disks in sequence, the other end of the structural backbone is securely connected to the distal fixing disk; the driving unit comprises a motor part, a motion conversion part and a plurality of linear motion mechanisms, wherein a sterile barrier is provided between the motion conversion part and the linear motion mechanisms; and the motor part comprises a first fixing plate and a first motor securely connected to the first fixing plate; and the motion conversion part comprises a plurality of transmission chains, each of the transmission chains converts a rotational output of the first motor into a linear motion of two output rods, the linear motion of the output rods is transferred to a push-pull rod at an input end of the linear motion mechanism through the sterile barrier, an output end of the linear motion mechanism is securely connected to one end of one driving backbone passing through the proximal spacing disks, and the other end of the driving backbone is securely connected to the proximal fixing disk.

Preferably, the number of the proximal structural segments is equal to the number of the distal structural segments.

In a preferred embodiment, the linear motion mechanism comprises a shaft securely connected between the two channel fixing plates, and a slider slidably connected to the shaft, the slider serves as the output end of the linear motion mechanism and is securely connected to the driving backbone, the slider is further securely connected to one end of the push-pull rod, and the other end of the push-pull rod passes through the channel fixing plate and is connected to the output rod via the sterile barrier.

In a preferred embodiment, the sterile barrier comprises a guide rod base and a guide rod slidably passing through the guide rod base, a rear end of the guide rod is provided with a first quick-locking head for connection with the output rod, and a front end of the guide rod base is provided with a second quick-locking head for connection with the push-pull rod; and a sterile membrane for isolating a sterilizable part from an unsterilized part of the flexible surgical instrument system is securely connected to an outer periphery of the sterile barrier.

In a preferred embodiment, the first quick-locking head comprises a screw seat, an insertion hole for having the output rod inserted therein is provided in the screw seat, the screw seat is further provided with a threaded hole in communication with the insertion hole, and a set screw is connected, in a matching manner, to the threaded hole.

In a preferred embodiment, the second quick-locking head comprises two sliders and an elastic ring, the two sliders are engaged together toward each other, the two sliders hold the elastic ring with straight slots on their respective left and right sides, the two sliders are each provided with a central hole, and the two sliders are each provided with a crescent-shaped projection in their respective central hole, the two crescent-shaped projections being arranged oppositely; and a rear end of the push-pull rod is provided with a first annular groove.

In a preferred embodiment, a sterile barrier housing is securely connected to an outer periphery of the guide rod base, a quick-locking disk is rotatably connected inside the sterile barrier housing, the quick-locking disk is located in front of the guide rod base, a circumferentially-distributed arc-shaped groove is provided on the quick-locking disk, and a plurality of pairs of semicircular protrusions are arranged on groove walls of the arc-shaped groove; and when the quick-locking disk is rotated, each pair of the semicircular protrusions respectively exerts lateral pressure on the two sliders on the second quick-locking head extending into the annular groove, to enlarge a hole formed by the two crescent-shaped projections on the sliders.

In a preferred embodiment, the flexible surgical instrument system further comprises a flexible surgical instrument connection housing, wherein the proximal structural body and the middle connecting body are both located inside the flexible surgical instrument connection housing; a rear end of the flexible surgical instrument connection housing is provided with a push-pull rod limiting disk, the push-pull rod limiting disk being rotatably connected inside the flexible surgical instrument connection housing, and a plurality of limiting holes through which the push-pull rods pass are provided in the push-pull rod limiting disk, the inner diameter of the limiting holes being larger than the diameter of the push-pull rods; and a second annular groove is provided at the same axial position on each push-pull rod, and the second annular groove is located in front of the first annular groove.

In a preferred embodiment, the sterile barrier comprises a guide rod base and a guide rod slidably passing through the guide rod base; the guide rod is connected between the output rod and the push-pull rod; and a sterile membrane for isolating a sterilizable part from an unsterilized part of the flexible surgical instrument system is securely connected to the guide rod base.

In a preferred embodiment, a rear end of the guide rod is provided with a first quick-locking head for connection with the output rod, the first quick-locking head comprises two second sliders and an elastic ring, the two second sliders are engaged together toward each other, the two second sliders hold the elastic ring with their respective straight slots on the left and right sides, the two second sliders are each provided with a central hole, and the two second sliders are each provided with a crescent-shaped projection in the respective central hole, the two crescent-shaped projections being arranged oppositely.

In a preferred embodiment, a front end of the guide rod is provided with a second quick-locking head for connection with the push-pull rod, a rear end of the push-pull rod is provided with an annular groove, the second quick-locking head is provided with a feature groove matching the shape of the rear end of the push-pull rod, and an opening of the feature groove is located at a side face of the second quick-locking head; and a flexible surgical instrument connection housing is provided on the outside of the middle connecting body, the middle connecting body and the proximal structural body are both located inside the flexible surgical instrument connection housing, and a front side of the guide rod base is provided with a quick-lock mechanism for connection with the flexible surgical instrument connection housing.

In a preferred embodiment, the quick-lock mechanism comprises a circumferential limiting block connected to the guide rod base via a restoring spring, an L-shaped first limiting groove is arranged on the outer side of the circumferential limiting block, a front side edge of the guide rod base is provided with a sterile barrier connection housing, and a front end of the sterile barrier connection housing is provided with a plurality of second limiting grooves extending circumferentially and having only one opening; a first projection feature configured to slide in the first limiting groove is provided on an inner side of a rear end of the flexible surgical instrument connection housing, and a second projection feature configured to slide in the second limiting groove is provided on an outer side of the rear end of the flexible surgical instrument connection housing; and when the first projection feature slides along a circumferential section of the first limiting groove to a position where an axial section is located, the second projection feature reaches the bottom of the second limiting groove, while the rear end of the push-pull rod enters into the feature groove of the second quick-locking head and forms a matching connection state with the feature groove of the second quick-locking head.

In a preferred embodiment, the motion conversion part further comprises a second fixing plate, a third fixing plate and a fourth fixing plate which are provided in front of the first fixing plate; and each of the transmission chains comprises a first threaded rod and a second threaded rod which are spaced apart and rotatably supported between the third fixing plate and the fourth fixing plate, and a rear end of the first threaded rod passes through the third fixing plate and the second fixing plate in sequence and is connected to an output shaft of the first motor via a coupling; a first gear is securely connected to the first threaded rod between the second fixing plate and the third fixing plate, the first gear is in transmission connection with a second gear via an idle gear, and the second gear is securely connected to the second threaded rod; a first nut and a second nut are respectively connected, in a matching manner, to the first threaded rod and the second threaded rod between the third fixing plate and the fourth fixing plate; and the two output rods are respectively securely connected to the first nut and the second nut, and front ends of the output rods pass through the fourth fixing plate.

In a preferred embodiment, a front end of the distal structural body is provided with a surgical end effector, an actuation wire of the surgical end effector passes through the distal structural body, and the other end thereof is connected to a surgical end effector driving mechanism located between the two channel fixing plates; the surgical end effector driving mechanism comprises a first surgical end effector push rod with a front end being securely connected to the actuation wire, a rear end of the first surgical end effector push rod is perpendicularly and securely connected to the middle of a second surgical end effector push rod, each of two ends of the second surgical end effector push rod is securely connected to one end of a second push-pull rod, and the other end of the second push-pull rod passes through the channel fixing plate and extends rearward; a second motor is securely connected to the first fixing plate, and the motion conversion part further comprises a second transmission chain which converts a rotational output of the second motor into a linear motion of two second output rods; and the linear motion of the second output rod is transferred to the second push-pull rod via the sterile barrier.

In a preferred embodiment, the motion conversion part further comprises a second fixing plate, a third fixing plate and a fourth fixing plate which are provided in front of the first fixing plate; and the second transmission chain comprises a third threaded rod, a rear end of the third threaded rod is connected to the second motor via a coupling between the first fixing plate and the second fixing plate, the third fixing plate and the fourth fixing plate jointly and rotatably support the third threaded rod, a third nut is connected, in a matching manner, to the third threaded rod between the third fixing plate and the fourth fixing plate, the third nut is securely connected to two rods, front ends of the two rods pass through the fourth fixing plate and jointly support a connection block, and the two output rods are securely connected to a front side of the connection block.

In a preferred embodiment, the flexible surgical instrument system further comprises a driving unit shell, wherein the first fixing plate is rotatably connected to the driving unit shell, an inner wall of the driving unit shell is securely connected to an inner ring gear, the first fixing plate is securely connected with a third motor, an output shaft of the third motor is securely connected with a gear, and the gear meshes with the inner ring gear.

In a preferred embodiment, the flexible surgical instrument system further comprises a driving unit shell and a linear module, wherein the linear module comprises a bracket body, a fourth motor securely connected to the bracket body, and a linear feed mechanism securely connected to an output shaft of the fourth motor; an output end of the linear feed mechanism is securely connected to the driving unit shell; and the fourth motor drives the driving unit shell by means of the linear feed mechanism, to drive the driving unit, the sterile barrier and the flexible surgical instrument to perform a linear motion.

In a preferred embodiment, the linear feed mechanism comprises a lead screw rotatably connected to the bracket body, the lead screw is sheathed with a third slider which is threadedly fitted with the lead screw, a linear sliding groove is provided on the bracket body, and the third slider is slidably provided in the linear sliding groove; and the output shaft of the fourth motor is securely connected to the lead screw via a coupling.

In a preferred embodiment, the spiral direction of the first threaded rod is different from that of the second threaded rod, and the pitch of the first threaded rod is the same as that of the second threaded rod.

The present invention has the following advantages due to utilizing the above technical solutions: 1. In the present invention, a flexible continuous body structure comprising a proximal structural body, a middle connecting body and a distal structural body is used as the main body and cooperates with a driving unit, wherein the distal structural body is linked to the proximal structural body via the middle connecting body, the driving unit is linked to the proximal structural body, and when the driving unit drives the proximal structural body to turn in any direction, the distal structural body correspondingly turns in the opposite direction, and a flexible surgical arm formed by the distal structural body and an envelope is thus capable of turning in any direction; 2. In the present invention, the driving unit comprises linear motion mechanisms, a motor part and a motion conversion part, wherein a push-pull rod of the linear motion mechanism is connected to the proximal structural body via a driving backbone, a transmission chain in the motion conversion part can convert an output of a motor in the motor part into a cooperative linear motion of two output rods, and the output rods are connected to the push-pull rod of the linear motion mechanism via a sterile barrier, thereby effectively isolating an unsterilized part from a sterilized part of the system, and ensuring the clinical practicability of surgery; 3. In the present invention, the sterile barrier comprises a guide rod, one end of the guide rod is connected to the output rod of the transmission chain via a quick-locking head, and the other end of the guide rod is connected to the push-pull rod of the linear motion mechanism via a second quick-locking head, thus enhancing the modularity and flexibility of the whole system; 4. In the present invention, a surgical end effector is provided in the front end of the distal structural body, a actuation wire of the surgical end effector passes through the distal structural body, and the other end is connected to a surgical end effector driving mechanism in the middle connecting body; and the motor part is provided with a motor for driving the push and pull of the actuation wire, and the output of the motor reaches the surgical end effector driving mechanism through another transmission chain, thereby implementing action control over the surgical end effector; 5. In the present invention, the inner wall of the driving unit shell is provided with an inner ring gear, the motor part is provided with a motor, an output end of the motor is connected to a gear meshing with the inner ring gear, and the motor can thus be used to drive the rotation of the parts, as a whole, other than the driving unit shell and the inner ring, thereby achieving control over the roll angle of the surgical end effector; and 6. The present invention is further provided with a linear module connected to the driving unit shell, so that the driving unit shell can be used to drive the driving unit, the sterile barrier and the flexible surgical instrument to perform a linear feed motion.

The present invention can be applied to the single-port laparoscopic surgery, and can also be applied to the natural orifice transluminal non-invasive surgery.

DETAILED DESCRIPTION OF EMBODIMENTS

The present invention is to be described in detail below with reference to the accompanying drawings and embodiments.

Figure 1:
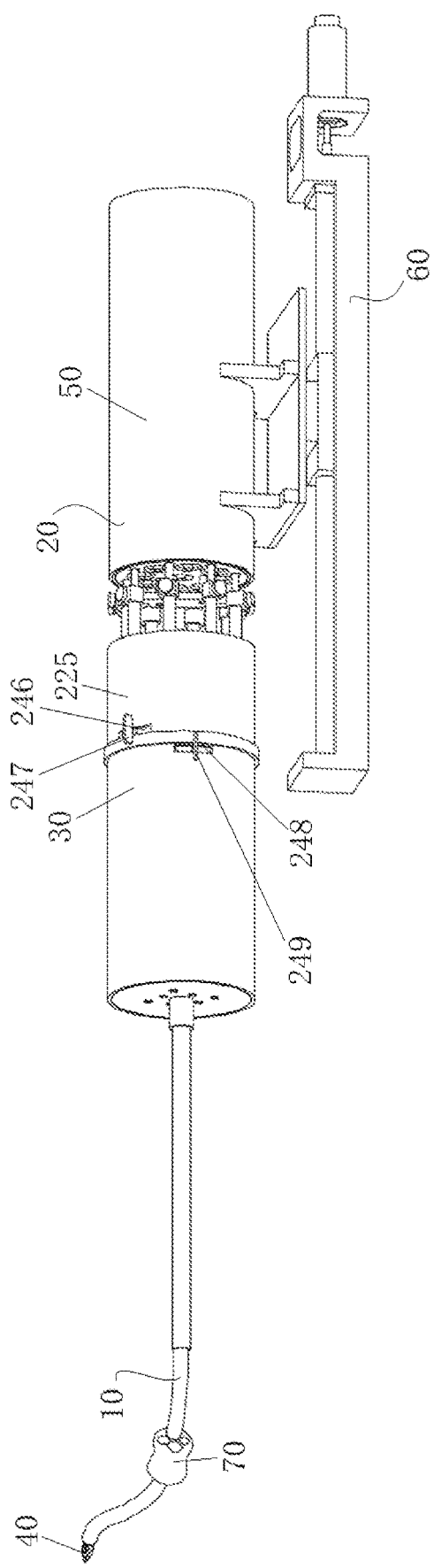
FIG. 1 is an overall structural schematic diagram according to the present invention when a first type of sterile barrier is used.
Figure 2:
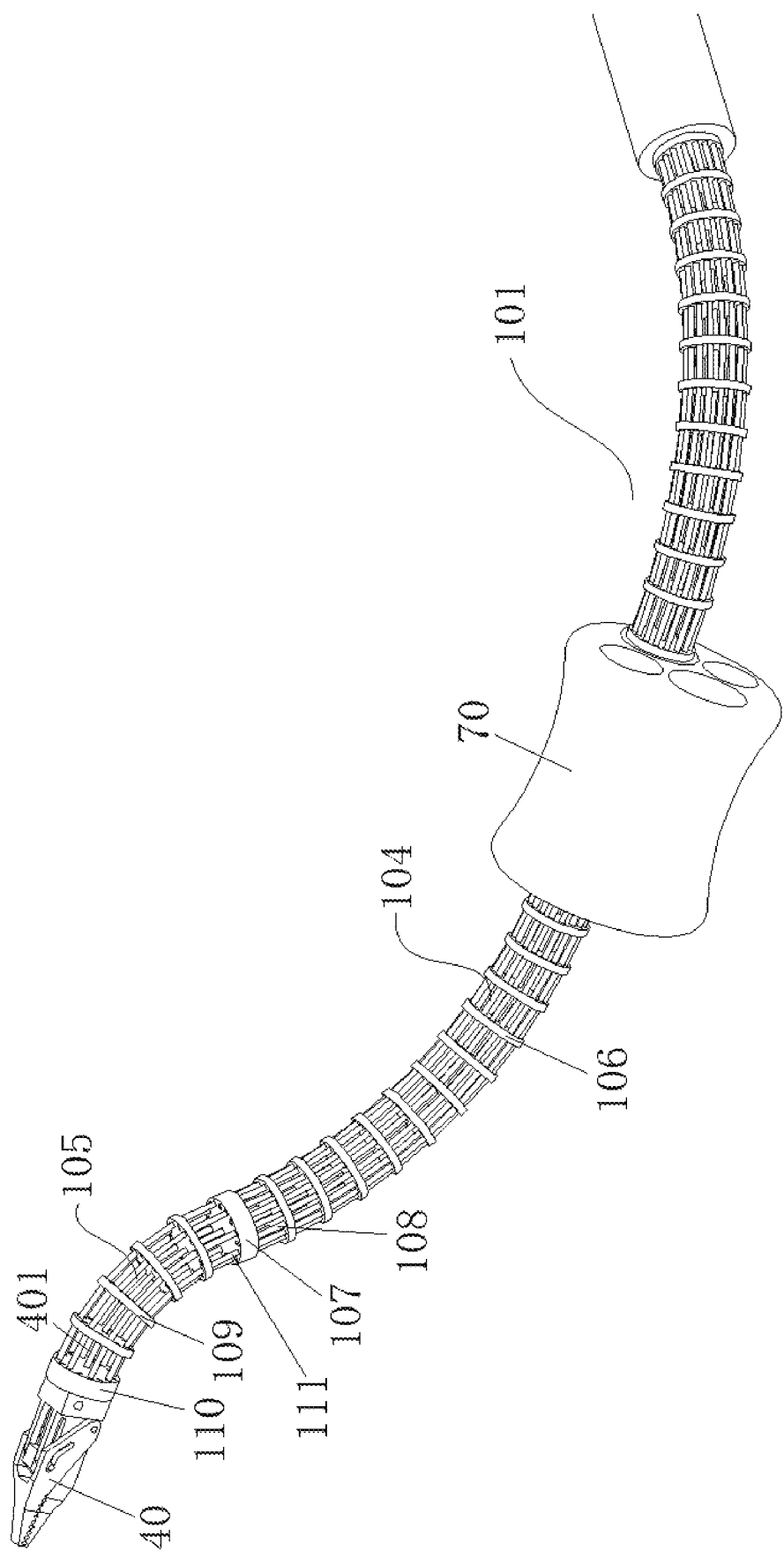
FIG. 2 is a structural schematic diagram of a distal structural body according to the present invention.
Figure 3:
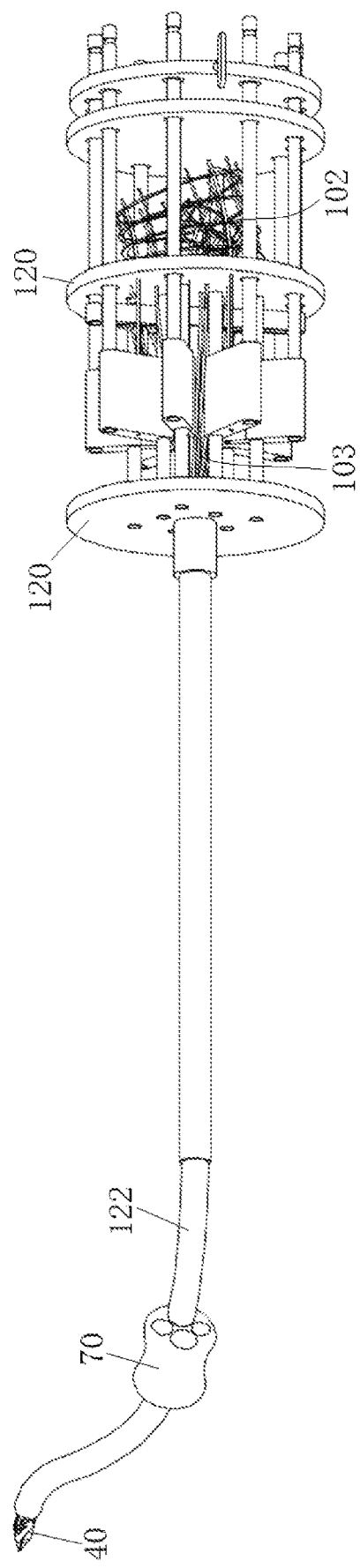
FIG. 3 is a structural schematic diagram of a flexible surgical instrument and a linear motion mechanism according to the present invention.
Figure 5:
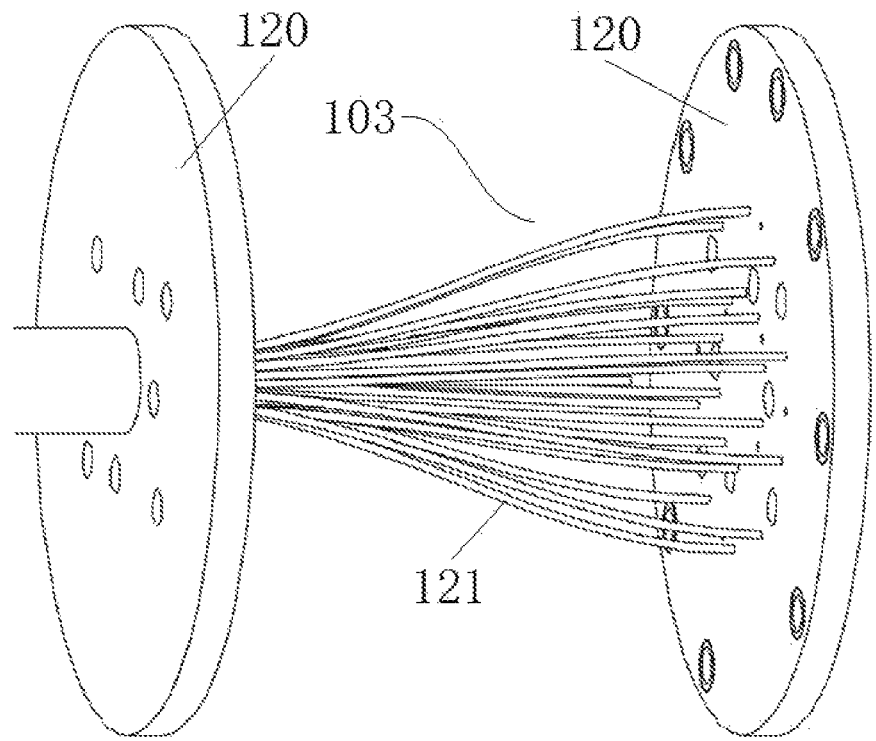
FIG. 5 is a structural schematic diagram of a middle connecting body according to the present invention.

As shown in FIG. 1, the present invention comprises a flexible surgical instrument 10 and a driving unit 20. The flexible surgical instrument 10 comprises a flexible continuous body structure composed of a distal structural body 101 (as shown in FIG. 2), a proximal structural body 102 (as shown in FIG. 3) and a middle connecting body 103 (as shown in FIG. 5). The distal structural body 101 is linked to the proximal structural body 102 via the middle connecting body 103; and the driving unit 20 is linked to the proximal structural body 102, and when the driving unit 20 drives the proximal structural body 102 to turn in any direction, the distal structural body 101 correspondingly turns in the opposite direction.

As shown in FIG. 2, the distal structural body 101 comprises a first distal structural segment 104 and a second distal structural segment 105. The first distal structural segment 104 comprises first distal spacing disks 106, a first distal fixing disk 107 and first segment structural backbones 108; and the second distal structural segment 105 comprises second distal spacing disks 109, a second distal fixing disk 110 and second segment structural backbones 111. The first distal spacing disks 106 and the second distal spacing disks 109 are respectively distributed at equal intervals in the first distal structural segment 104 and the second distal structural segment 105, in order to prevent the first segment structural backbones 108 and the second segment structural backbones 111 from being destabilized when being pushed.

Figure 4:
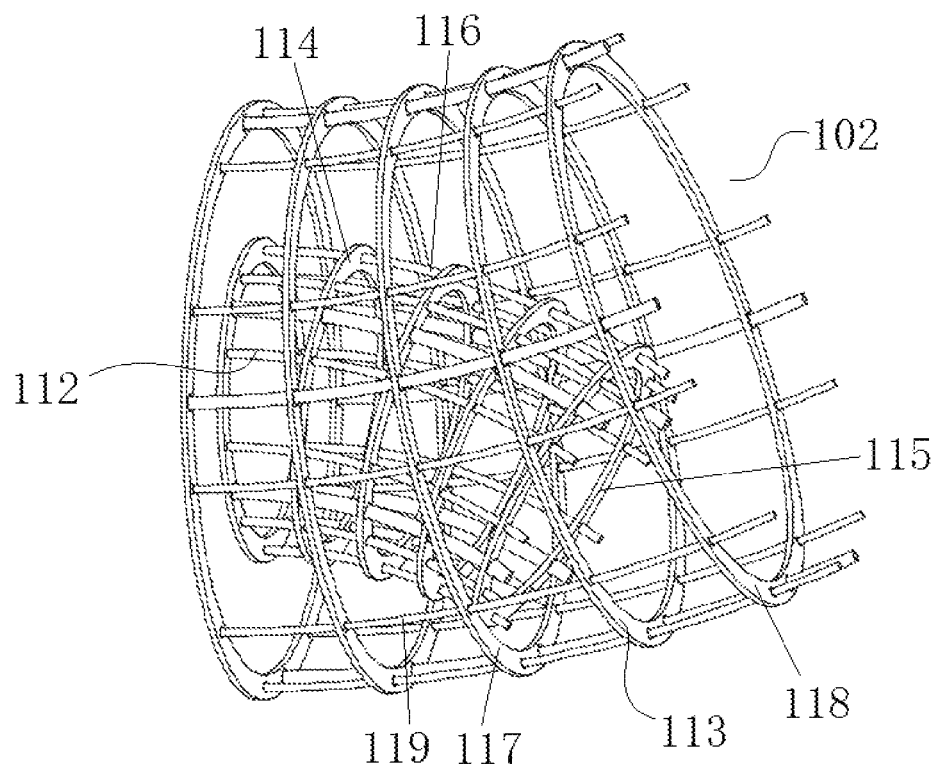
FIG. 4 is a structural schematic diagram of a proximal structural body according to the present invention.

As shown in FIGS. 3 and 4, the proximal structural body 102 comprises a first proximal structural segment 112 and a second proximal structural segment 113. The first proximal structural segment 112 comprises first proximal spacing disks 114, a first proximal fixing disk 115 and first segment structural backbones 116; and the second proximal structural segment 113 comprises second proximal spacing disks 117, a second proximal fixing disk 118, and second segment structural backbones 119. The first proximal spacing disks 114 and the second proximal spacing disks 117 are respectively distributed at intervals in the first proximal structural segment 112 and the second proximal structural segment 113, in order to prevent the first segment structural backbones 116 and the second segment structural backbones 119 from being destabilized when being pushed. The first segment structural backbones 116 on the first proximal structural segment 112 are securely connected, in one-to-one correspondence, to or are the same as the first segment structural backbones 108 on the first distal structural segment 104; and the second segment structural backbones 119 on the second proximal structural segment 113 are securely connected, in one-to-one correspondence, to or are the same as the second segment structural backbones 111 on the second distal structural segment 105. For each of the proximal structural segments 112, 113 and each of the distal structural segments 104, 105, the number of the structural backbones is three or more.

As shown in FIG. 5, the middle connecting body 103 comprises two channel fixing plates 120 and structural backbone guide channels 121 fixedly connected between the two channel fixing plates 120. One end of the first segment structural backbone 116 (108) is securely connected to the first proximal fixing disk 115, and the other end thereof passes through the first proximal spacing disks 114, the structural backbone guide channel 121 and the first distal spacing disks 106 in sequence and is then securely connected to the first distal fixing disk 107. One end of the second segment structural backbone 119 (111) is securely connected to the second proximal fixing disk 118, and the other end thereof passes through the second proximal spacing disks 117, the structural backbone guide channel 121, the first distal structural segment 104 and the second distal spacing disks 109 in sequence and is then securely connected to the second distal fixing disk 110. The structural backbone guide channel 121 functions to maintain the shape of the structural backbone under a pushing or pulling force. A flexible surgical instrument connection housing 30 is provided on the outside of the middle connecting body 103, the middle connecting body 103 and the proximal structural body 102 of the flexible surgical instrument 10 are both located inside the flexible surgical instrument connection housing 30, and the two channel fixing plates 120 are securely connected to the flexible surgical instrument connection housing 30.

The number of the distal structural segments comprised in the distal structural body 101 and the number of the proximal structural segments comprised in the proximal structural body 102 may also be one or more than two, but the number of the proximal structural segments must be equal to the number of the distal structural segments. In addition, when the number of the distal structural segments comprised in the distal structural body 101 is two or more, the distal structural segments are connected in series, that is, the second segment structural backbone passes through the first distal fixing disk and the first distal spacing disks (and can also pass through the first segment structural backbone if the first segment structural backbone is of a tubular structure); and when the number of the proximal structural segments comprised in the proximal structural body 102 is two or more, series connection, parallel arrangement or nested arrangement (as shown in FIG. 4), etc. may be used between the structural segments.

Figure 6:
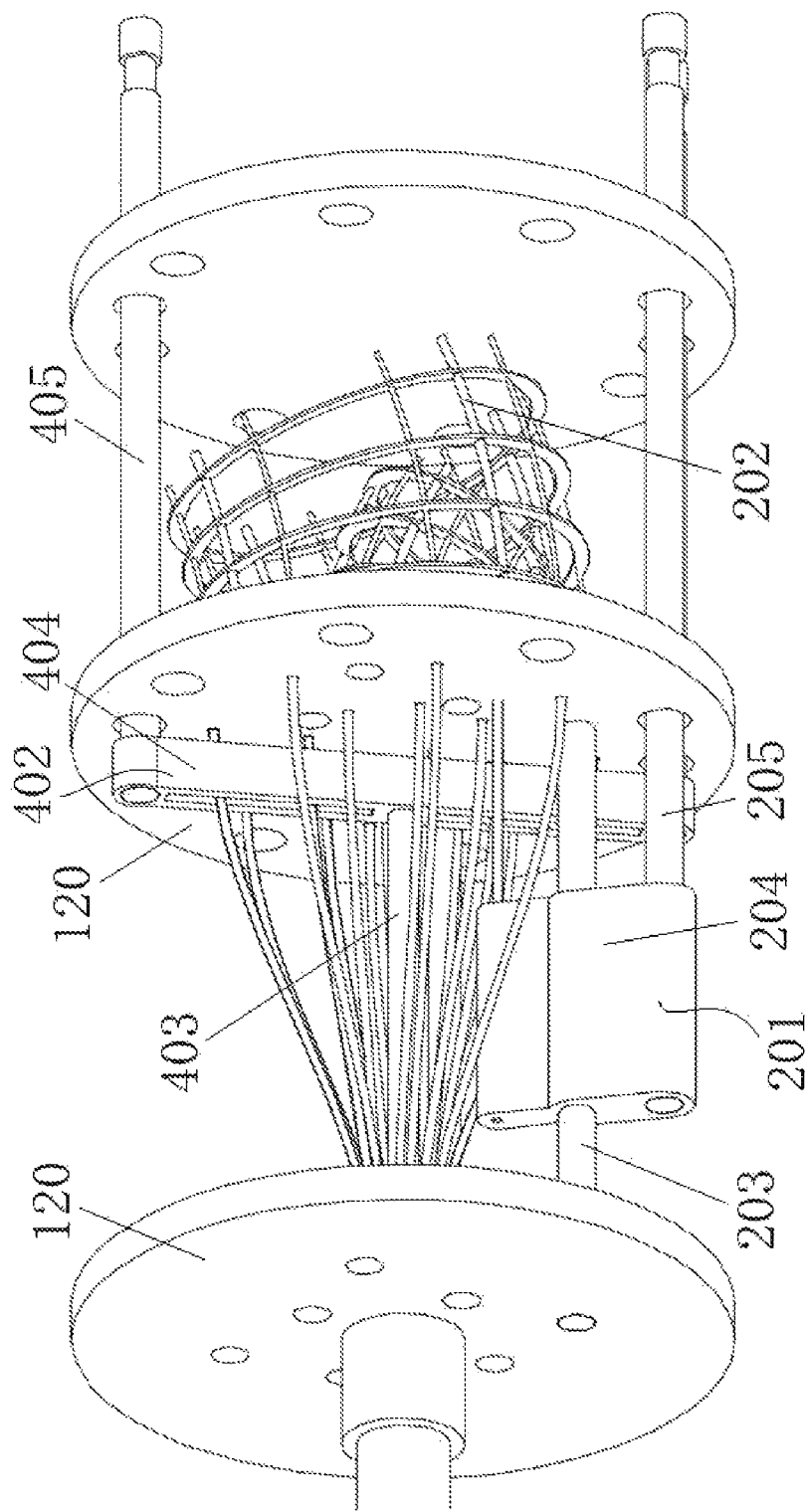
FIG. 6 is a structural schematic diagram of a linear motion mechanism and a surgical end effector driving mechanism according to the present invention.

The driving unit 20 comprises a plurality of linear motion mechanisms 201 (as shown in FIGS. 3 and 6) provided between the two channel fixing plates 120, each of the linear motion mechanisms 201 comprises one push-pull rod 205 and one slider 204 securely connected to the push-pull rod 205, the slider 204 is securely connected to one end of one driving backbone 202, the other end of the driving backbone 202 passes through the first proximal spacing disks 114 and is then securely connected to the first proximal fixing disk 115, or passes through the second proximal spacing disks 117 and is then securely connected to second proximal fixing disk 118. In this embodiment, eight driving backbones 202 are provided, four of which are securely connected to the first proximal fixing disk 115, and the other four are connected to the second proximal fixing disk 118. The linear motion mechanisms 201 cooperatively push/pull the driving backbones 202 connected to the first proximal structural segment 112, so that the degree of freedom of turning of the first proximal structural segment 112 in any direction can be achieved, and when the first proximal structural segment 112 is turned in a certain direction, the first distal structural segment 104 will be turned in an opposite direction in a certain proportional relationship (determined jointly by the distribution radii of the first segment structural backbone 116 and the first segment structural backbone 108). Similarly, the linear motion mechanisms 201 cooperatively push/pull the driving backbones 202 connected to the second proximal structural segment 113, so that the degree of freedom of turning of the second proximal structural segment 113 in any direction can be achieved, and when the second proximal structural segment 113 is turned in a certain direction, the second distal structural segment 105 will be turned in an opposite direction in a certain proportional relationship (determined jointly by the distribution radii of the second segment structural backbone 119 and the second segment structural backbone 111).

As shown in FIG. 6, the linear motion mechanism 201 further comprises a shaft 203 fixedly connected between the two channel fixing plates 120. The slider 204 is slidably connected to the shaft 203. The push-pull rod 205 passes through the channel fixing plate 120 and extends backward.

Figure 7:
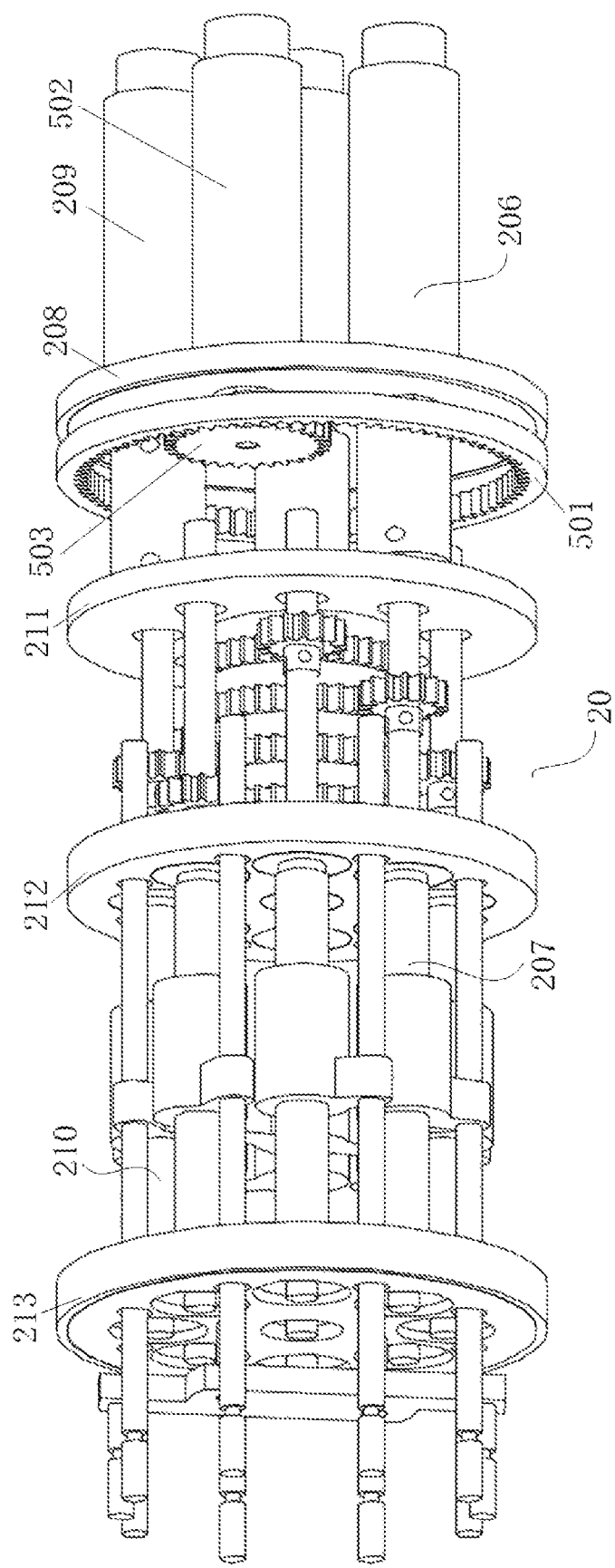
FIG. 7 is a structural schematic diagram of a motor part and a motion conversion part of a driving unit according to the present invention.
Figure 8:
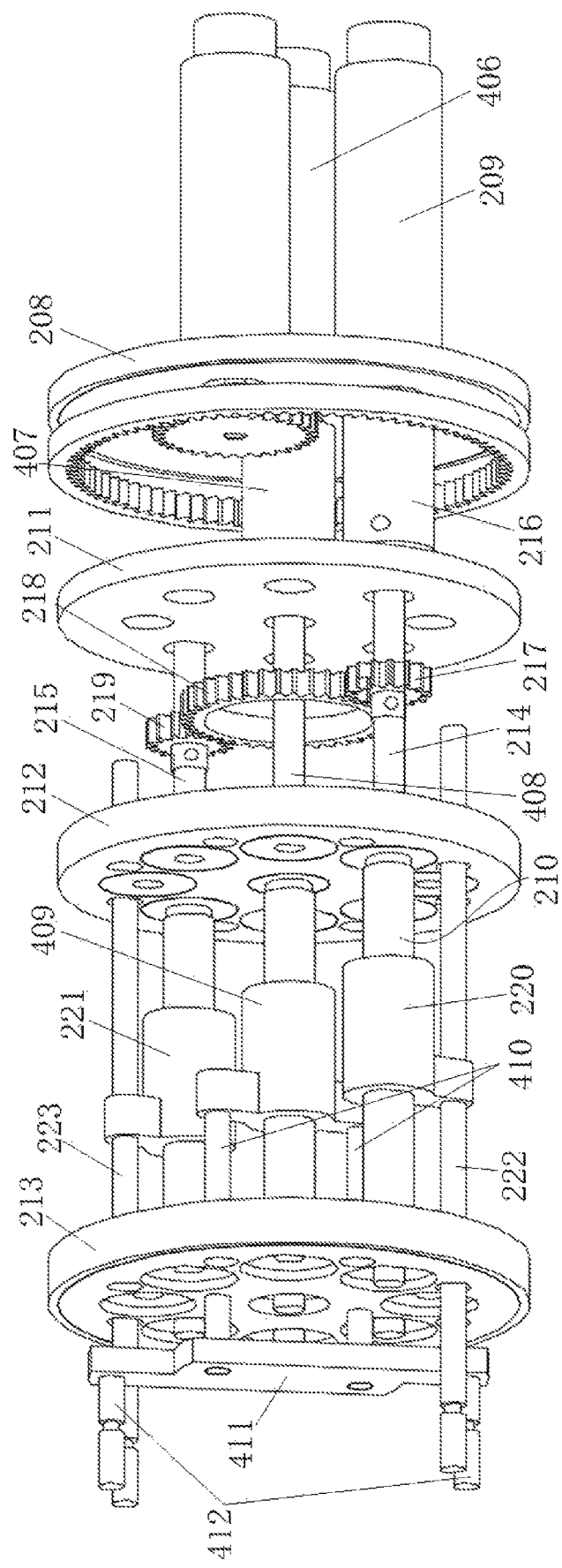
FIG. 8 is a structural schematic diagram of a transmission chain and a second transmission chain according to the present invention.

As shown in FIGS. 7 and 8, the driving unit 20 further comprises a motor part 206 and a motion conversion part 207, wherein the motor part 206 comprises a first fixing plate 208 and a plurality of (four in this embodiment) motors 209, which are securely connected to the first fixing plate 208 and are used for supplying driving forces to the driving backbones 202. The motion conversion part 207 comprises a plurality of (four in this embodiment) transmission chains 210, each of the transmission chains 210 converts a rotational output of one motor 209 into a linear motion of two output rods 222, 223, and the linear motion of the two output rods 222, 223 are ultimately transferred to two push-pull rods 205 respectively, thereby driving a pair of driving backbones 202 to complete cooperative pushing or pulling movement.

As shown in FIGS. 7 and 8, the motion conversion part 207 further comprises a second fixing plate 211, a third fixing plate 212 and a fourth fixing plate 213 which are provided in front of the first fixing plate 208. Each of the transmission chains 210 comprises a first threaded rod 214 and a second threaded rod 215 which are spaced apart from each other and rotationally supported between the third fixing plate 212 and the fourth fixing plate 213, wherein one end of the first threaded rod 214 passes through the third fixing plate 212 and the second fixing plate 211 in sequence and is connected to an output shaft of the respective motor 209 via a coupling 216. A first gear 217 is securely connected to the first threaded rod 214 between the second fixing plate 211 and the third fixing plate 212; and the first gear 217 is in transmission connection with a second gear 219 via an idle gear 218, the second gear 219 is securely connected to the second threaded rod 215, and one end of the second threaded rod 215 passes through the third fixing plate 212. The spiral direction of the first threaded rod 214 must be different from that of the second threaded rod 215, for example, the first threaded rod 213 and the second threaded rod 214 are respectively a left-handed threaded rod and a right-handed threaded rod, and preferably, the pitch of the first threaded rod 213 is the same as that of the second threaded rod 214. A first nut 220 and a second nut 221 are respectively connected, in a matching manner, to the first threaded rod 214 and the second threaded rod 215 between the third fixing plate 212 and the fourth fixing plate 213, the first nut 220 is securely connected to the output rod 222, and the second nut 221 is securely connected to the output rod 223. The output rod 222 and the output rod 223 pass through the fourth fixing plate 213 to serve as an output end of the transmission chain 210.

Figure 9:
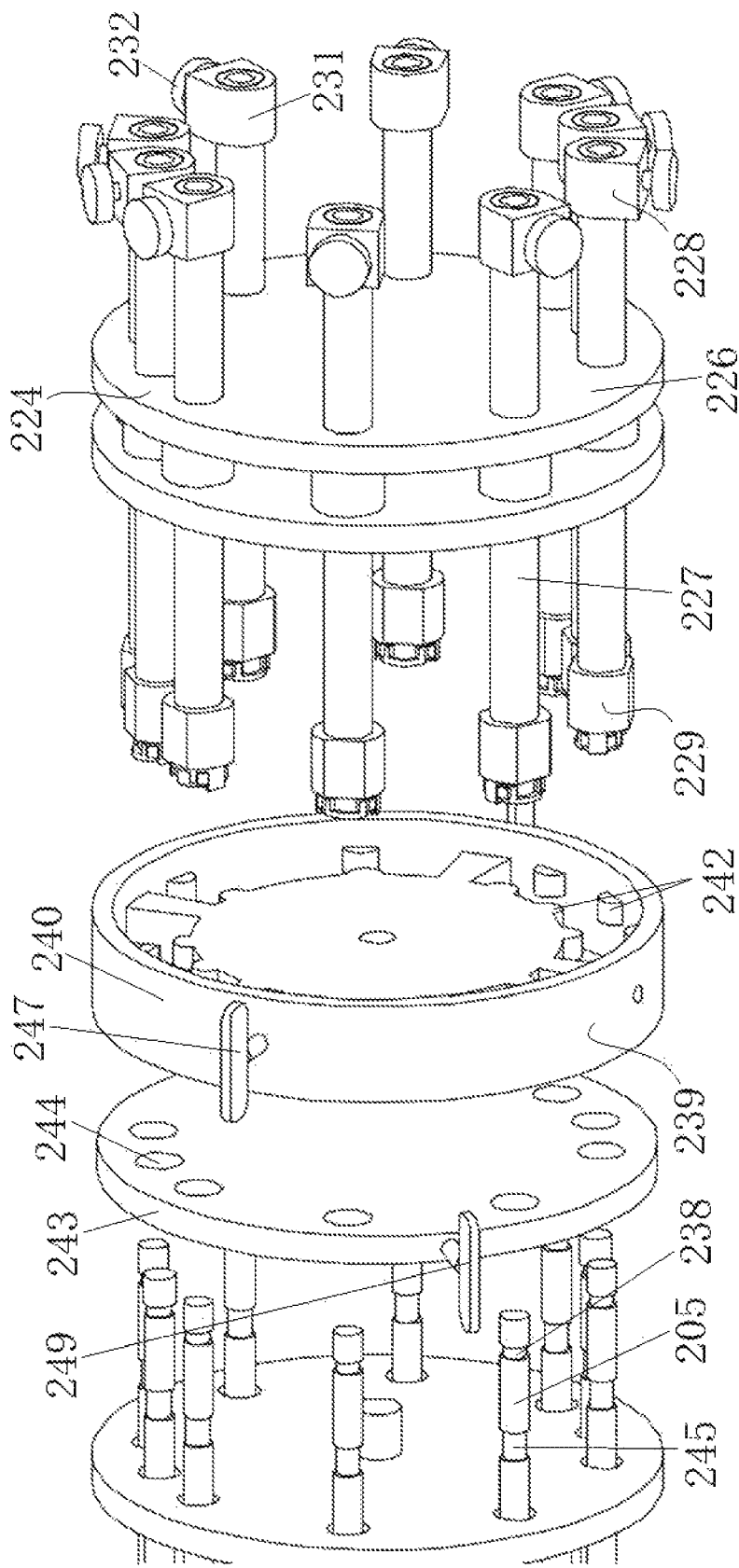
FIG. 9 is a structural schematic diagram of the first type of sterile barrier and its quick-locking mechanism according to the present invention, with a sterile barrier housing being removed.
Figure 10:
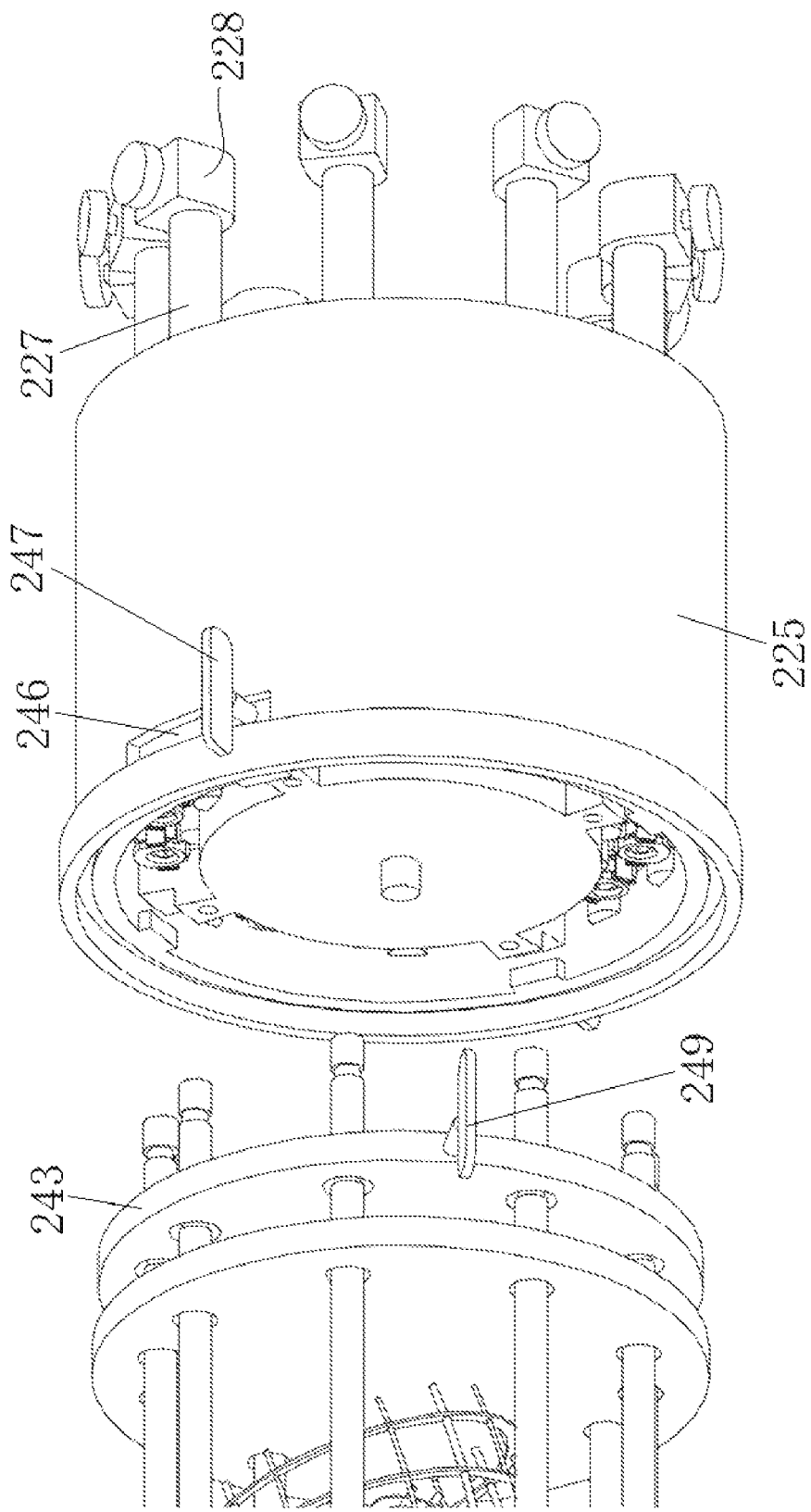
FIG. 10 is a structural schematic diagram showing the connection of the first type of sterile barrier and its quick-locking mechanism according to the present invention.
Figure 11:
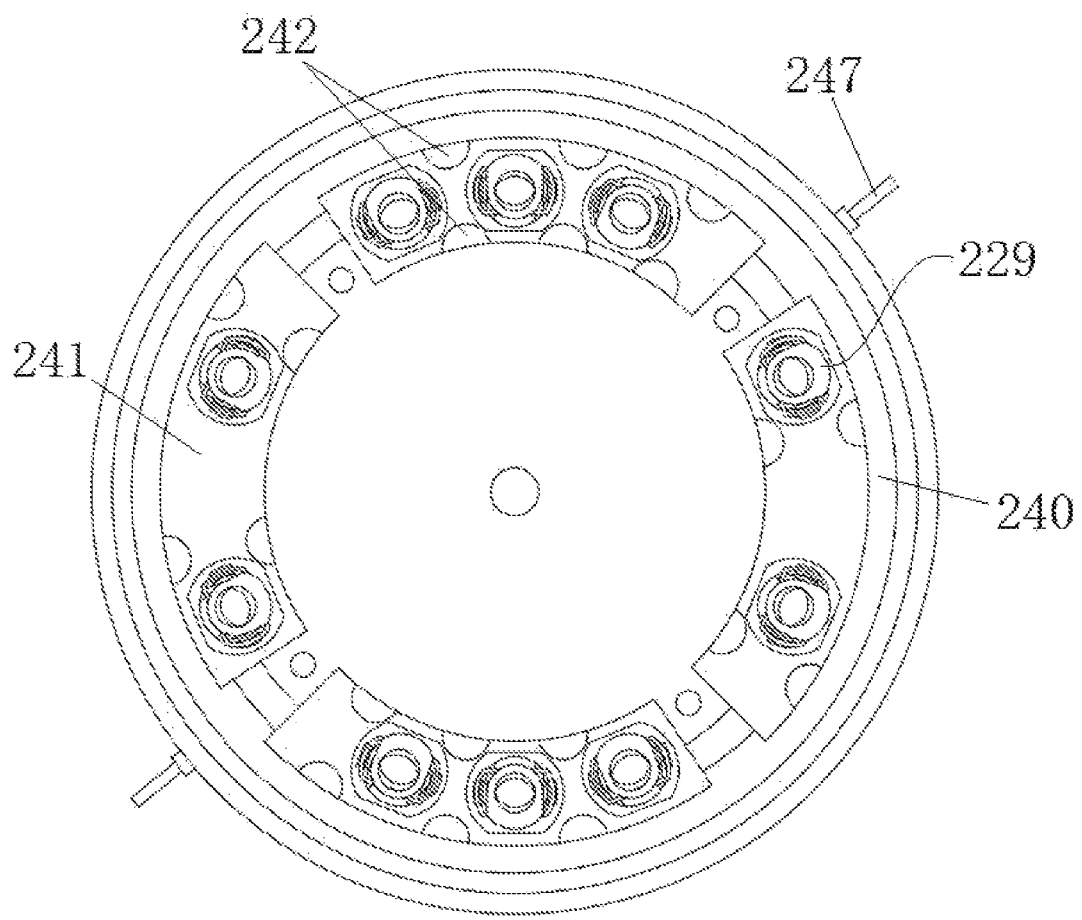
FIG. 11 is a structural schematic diagram of the first type of sterile barrier according to the present invention, viewed from another angle.
Figure 12:
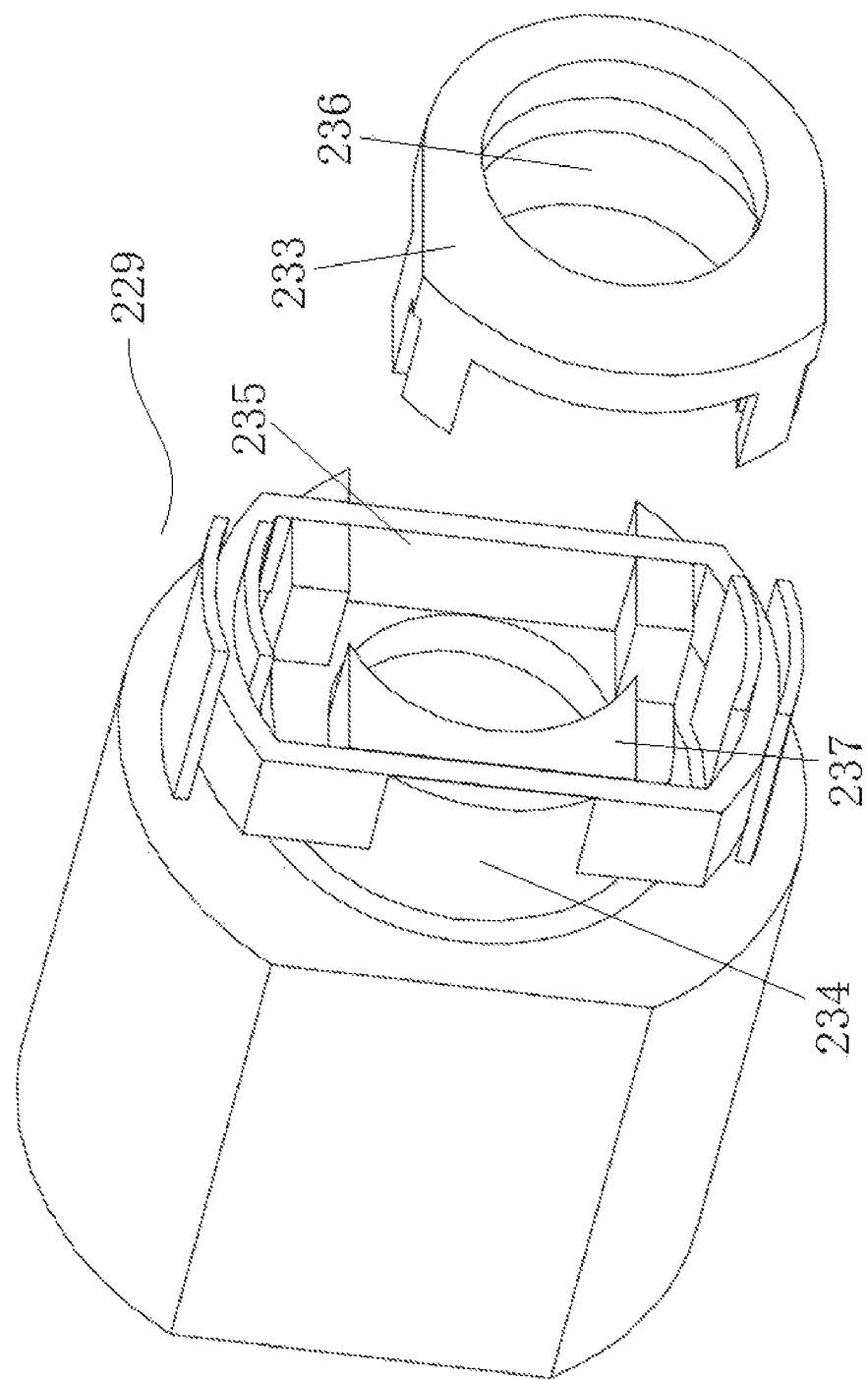
FIG. 12 is an explosive structural schematic diagram of a second quick-locking head of the first type of sterile barrier according to the present invention.
Figure 13:
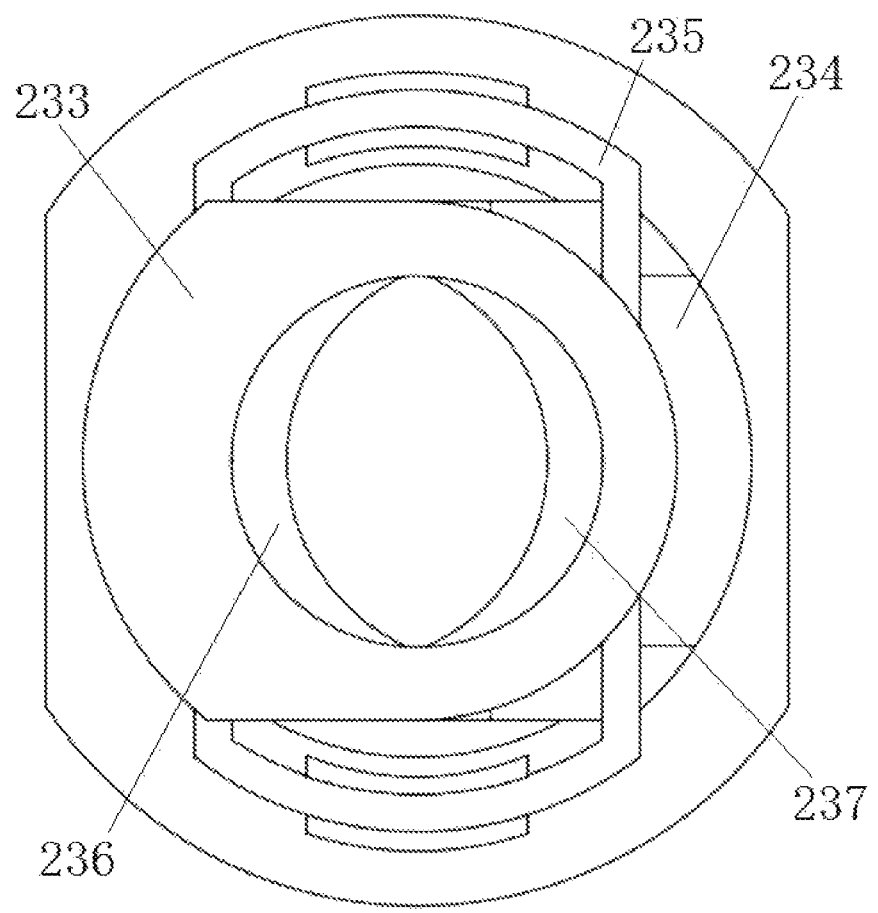
FIG. 13 is a structural schematic diagram of the second quick-locking head of the first type of sterile barrier according to the present invention, viewed from another angle.

As shown in FIG. 1, the linear motion mechanism 201 and the motion conversion part 207 of the driving unit 20 are connected via a sterile barrier 224. The present invention provides the structural designs of two types of sterile barriers, which are respectively described below:

As shown in FIGS. 1 and 9-11, the first type of sterile barrier 224 comprises a sterile barrier housing 225, a guide rod base 226 securely arranged in the sterile barrier housing 225, a guide rod 227 slidably passing through the guide rod base 226, a first quick-locking head 228 arranged at the rear end of the guide rod 227 for connection with the output rod 222 or the output rod 223 of the transmission chain 210, and a second quick-locking head 229 arranged at the front end of the guide rod 227 for connection with the push-pull rod 205. A sterile membrane (not shown) is securely connected to the outer periphery of the sterile barrier 224, and is configured to isolate sterilizable parts (such parts as the flexible surgical instrument 10 and the linear motion mechanism 201, which are located in front of the sterile barrier 223) from unsterilized parts (such parts as the motion conversion part 207, the motor part 206 and a linear module 50, which are located behind the sterile barrier 223), thereby ensuring the clinical practicability of surgery. The first quick-locking head 228 comprises a screw seat 231, an insertion hole for having the output rod 222 or the output rod 223 inserted therein is provided in the screw seat 231, the screw seat 231 is further provided with a threaded hole in communication with the insertion hole, and a set screw 232 is connected, in a matching manner, to the threaded hole. The quick connection between the guide rod 227 and the output rod 222 or the output rod 223 can be achieved by means of the first quick-locking head 228, wherein, when connecting, it is only necessary to insert the front end of the output rod 222 or the output rod 223 into the insertion hole of the corresponding screw seat 231, and then to rotate the set screw 232 to abut the head of the set screw 232 against the output rod 222 or the output rod 223. As shown in FIGS. 12 and 13, the second quick-locking head 229 comprises two sliders 233, 234 and an elastic ring 235, wherein the two sliders 233, 234 are identical in structure and are engaged together toward each other, and the two sliders 233, 234 hold the elastic ring 235 with straight slots on their respective left and right sides. The two sliders 233, 234 are each provided with a central hole, and the two sliders 233, 234 are each provided with a crescent-shaped projection 236, 237 in the respective central hole, the two crescent-shaped projections 236, 237 being arranged oppositely. The locked state of the second quick-locking head 229 of the present invention is as shown in FIG. 13, when the two sliders 233, 234 are subjected to lateral pressure, the elastic ring 235 is deformed, so that the sliders 233, 234 are respectively moved in the direction of the respective forces acting thereon. At this time, the two crescent-shaped projections 236, 237 move away from each other, the centers of the two crescent-shaped projections 236, 237 tend to coincide, and the formed hole is enlarged. When the two crescent-shaped projections 236, 237 form a closed circular hole, the push-pull rod 205 can be inserted into the second quick-locking head 229, and after the pressure is removed, the elastic ring 235 is restored by its own elasticity, thereby pushing the two sliders 233, 234 to move the two crescent-shaped projections 236 and 237 toward each other, and forming a clamping force on the push-pull rod 205. The rear end of the push-pull rod 205 is provided with a first annular groove 238, and when the two crescent-shaped projections 236, 237 are retained in the first annular groove 238 of the push-pull rod 205, the guide rod 227 can be securely connected to the push-pull rod 205. Similarly, the push-pull rod 205 can be easily pulled out by exerting lateral pressure on the two sliders 233, 234. To enable simultaneous locking connection of the push-pull rods 205 and the respective guide rods 227 to improve the installation efficiency of the system, the present invention is further provided with a quick-locking mechanism 239 for realizing quick locking of the push-pull rods 205 and the guide rods 227. As shown in FIGS. 9 and 11, the quick-locking mechanism 239 comprises a quick-locking disk 240 rotatably connected inside the sterile barrier housing 225, circumferentially-distributed arc-shaped grooves 241 are provided on the quick-locking disk 240, each second quick-locking head 229 extends into the respective arc-shaped groove 241, and a plurality of pairs of semicircular protrusions 242 are provided on groove walls of the arc-shaped groove 241, and each pair of semicircular protrusions 242 respectively exerts lateral pressure on the slider 233 and the slider 234 of the second quick-locking head 229 when the quick-locking disk 240 is rotated, so as to enlarge the hole formed by the two crescent-shaped projections 236, 237 on each second quick-locking head 229, to facilitate insertion of each push-pull rod 205.

Further, as shown in FIGS. 1, 9 and 10, the rear end of the flexible surgical instrument connection housing 30 is provided with a push-pull rod limiting disk 243, the push-pull rod limiting disk 243 being rotatably connected inside the flexible surgical instrument connection housing 30, and a plurality of limiting holes 244 through which the push-pull rods 205 pass are provided in the push-pull rod limiting disk 243, the inner diameter of the limiting holes 244 being larger than the diameter of the push-pull rods 205. A second annular groove 245 is provided at the same axial position on each push-pull rod 205, and the second annular groove 245 is located in front of the first annular groove 238. When it is necessary to quickly connect the sterile barrier 224 to each push-pull rod 205, firstly the axial position of each push-pull rod 205 is adjusted to align the second annular groove 245 with the limiting hole 244, and the push-pull rod limiting disk 243 is then rotated, and each of the limiting holes 244 is retained in the second annular groove 245 of the respective push-pull rod 205. At this time, the push-pull rods 205 are locked in the axial direction to facilitate simultaneous insertion of the respective second quick-locking heads 229.

Further, as shown in FIG. 10, a sliding groove 246 extending circumferentially is provided on the sterile barrier housing 225, and a trigger 247 securely connected to the quick-locking disk 240 is slidably provided in the sliding groove 246, so that the quick-locking disk 240 can be driven to rotate more easily by using the trigger 247. Correspondingly, as shown in FIG. 1, a sliding groove 248 extending circumferentially is provided on the flexible surgical instrument connection housing 30, and a trigger 249 securely connected to the push-pull rod limiting disk 243 is slidably provided in the sliding groove 248, so that the push-pull rod limiting disk 243 can be driven to rotate more easily by using the trigger 249.

Figure 14:
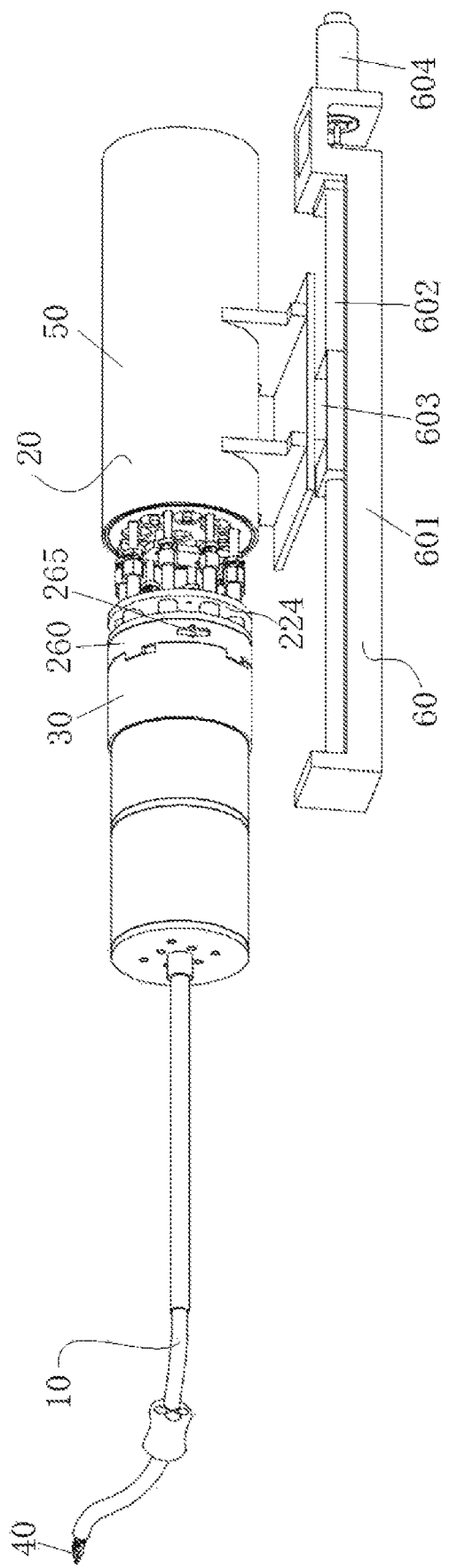
FIG. 14 is an overall structural schematic diagram according to the present invention, using a second type of sterile barrier.
Figure 15:
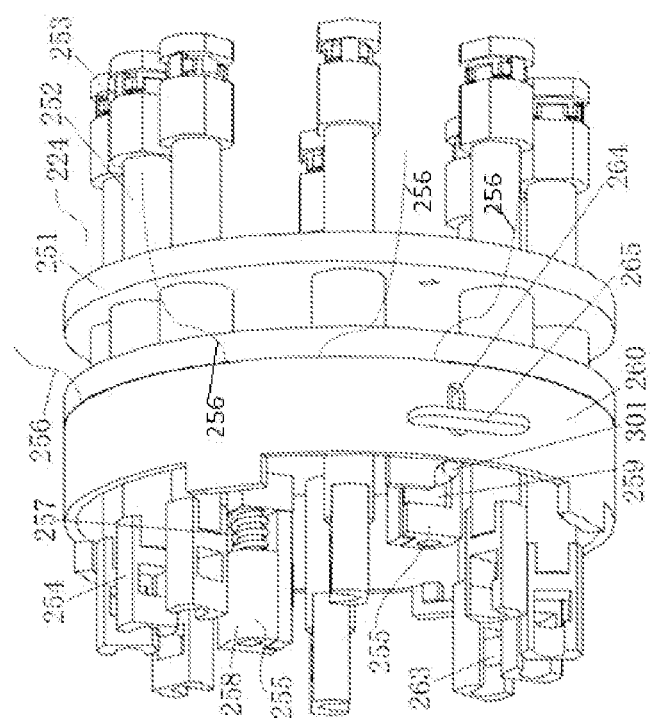
FIG. 15 is a structural schematic diagram of a second type of sterile barrier according to the present invention.
Figure 16:
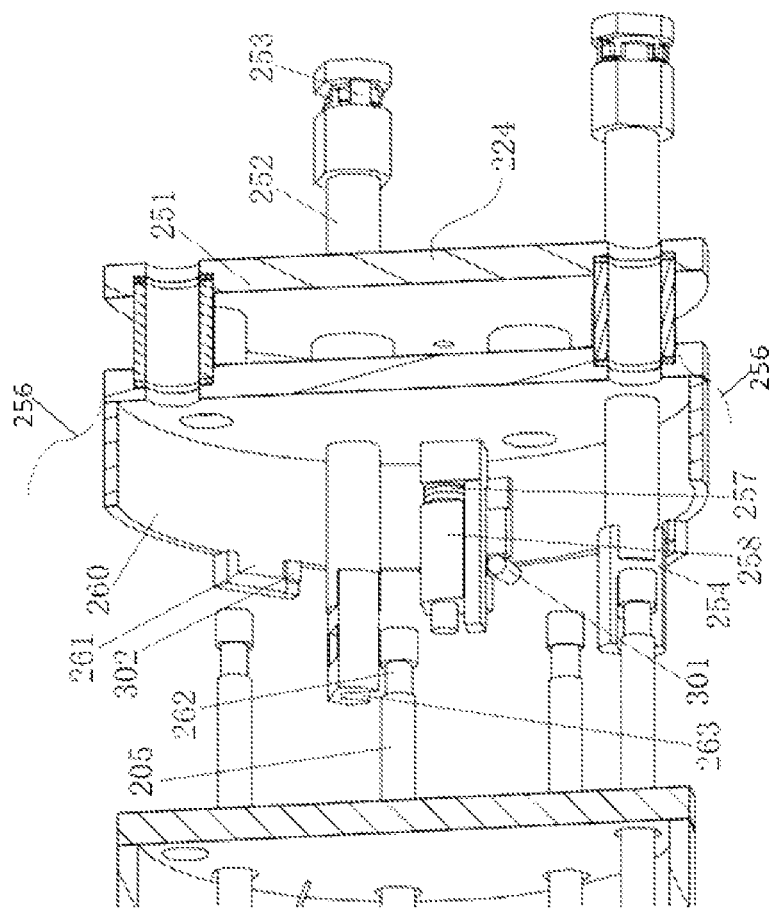
FIG. 16 is a structural schematic diagram showing the connection of the second type of sterile barrier and a push-pull rod according to the present invention.

As shown in FIGS. 14-16, the second type of sterile barrier 224 comprises a guide rod base 251, a guide rod 252 slidably passing through the guide rod base 251, a first quick-locking head 253 arranged at the rear end of the guide rod 252 for connection with the output rod 222 or the output rod 223 of the transmission chain 210, a second quick-locking head 254 arranged at the front end of the guide rod 252 for connection with the push-pull rod 205, and a quick-lock mechanism 255 provided on the front side of the guide rod base 251 for connection with the flexible surgical instrument connection housing 30. A sterile membrane 256 is securely connected to the guide rod base 251, and is configured to isolate sterilizable parts (such parts as the flexible surgical instrument 10 and the linear motion mechanism 201, which are located in front of the sterile barrier 223) from unsterilized parts (such parts as the motion conversion part 207, the motor part 206 and a linear module 50, which are located behind the sterile barrier 223), thereby ensuring the clinical practicability of surgery.

The quick-lock mechanism 255 comprises a circumferential limiting block 258 slidably arranged on the guide rod base 251 and connected to the guide rod base 251 via a restoring spring 257, and an L-shaped first limiting groove 259 is arranged on the outer side of the circumferential limiting block 258. A front side edge of the guide rod base 251 is provided with a sterile barrier connection housing 260, and the front end of the sterile barrier connection housing 260 is provided with a plurality of second limiting grooves 261 distributed circumferentially and having only one opening. The rear end of the push-pull rod 205 is provided with an annular groove 262, the second quick-locking head 254 is provided with a feature groove 263 matching the shape of the rear end of the push-pull rod 205, and an opening of the feature groove 263 is located at a side face of the second quick-locking head 254 so that the rear end of the push-pull rod 205 can enter into the feature groove 263 from one side of the second quick-locking head 254.

Figure 17:
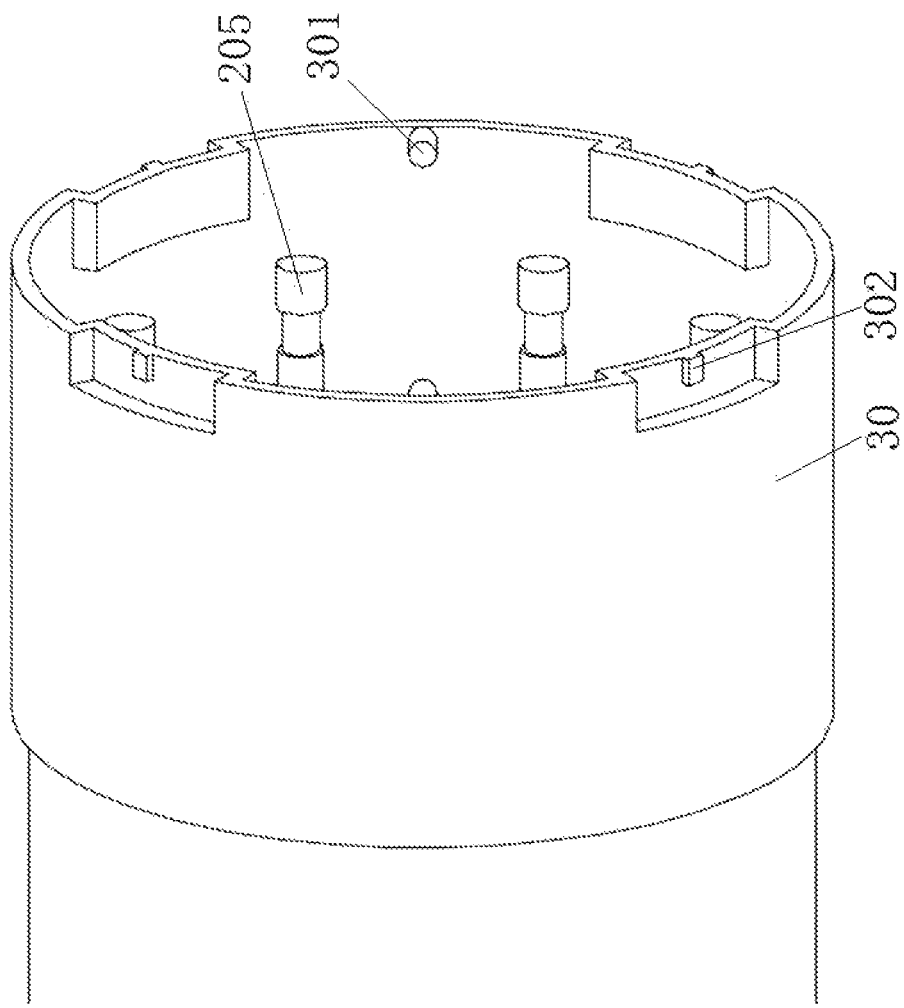
FIG. 17 is a structural schematic diagram of the rear end of a flexible surgical instrument connection housing matching the second type of sterile barrier according to the present invention.

In the present invention, the process of connecting the flexible surgical instrument connection housing 30 and the push-pull rod 205 to the sterile barrier 224 is as follows: a first projection feature 301 is provided on the inner side of the rear end of the flexible surgical instrument connection housing 30, a second projection feature 302 (as shown in FIG. 17) is provided on the outer side of the rear end of the flexible surgical instrument connection housing 30, the first projection feature 301 of the flexible surgical instrument connection housing 30 abuts against one side of the circumferential end of the first limiting groove 259 on the circumferential limiting block 258 and axially squeezes the circumferential limiting block 258, and the restoring spring 257 is compressed until an end face of the flexible surgical instrument connection housing 30 abuts against an end face of the sterile barrier connection housing 260, at this time, the second projection feature 302 on the outer side of the flexible surgical instrument connection housing 30 reaches the opening of the second limiting groove 261, while the rear end of each push-pull rod 205 is located on the side face of the second quick-locking head 254 and aligned with the opening of the feature groove 263 (as shown in FIG. 16); then, under the guidance of the second limiting groove 261, the flexible surgical instrument connection housing 30 is circumferentially rotated to the extreme position, at this time, the second projection feature 302 on the flexible surgical instrument connection housing 30 slides along the second limiting groove 261 to the end, while the rear end of each push-pull rod 205 enters the feature groove 263 on the second quick-locking head 254, so that the push-pull rod 205 and the guide rod 252 are axially connected, at this time, the first projection feature 301 of the flexible surgical instrument connection housing 30 enters into the junction of a circumferential section and an axial section of the first limiting groove 259; and since the first projection feature 301 no longer squeezes the circumferential limiting block 258 at this time, the circumferential limiting block 258 springs up in the direction away from the guide rod base 251 under the effect of the restoring spring 257, so that the first projection feature 301 enters into the bottom of the axial section of the first limiting groove 259, at which point the connection between the flexible surgical instrument connection housing 30 and the sterile barrier connection housing 260, and the connection between each push-pull rod 205 and the second quick-locking head 254 are completed.

The process of removing the flexible surgical instrument connection housing 30 and its internal structure from the sterile barrier 224 is the reverse of the above installation process: an axially-distributed elongated groove 264 is arranged on the sterile barrier connection housing 260, a trigger 265 is slidably arranged in the elongated groove 264, and one end of the trigger 265 passes through the elongated groove 264 and is securely connected to the circumferential limiting block 258. When the flexible surgical instrument connection housing 30 needs to be removed, the other end of the trigger 265 is firstly pushed axially to move the circumferential limiting block 258 in a direction approaching the guide rod base 251 and compresses the restoring spring 257, in this process, the first projection feature 301 moves along the axial section of the first limiting groove 259, and when the first projection feature 301 slides to the junction of the circumferential section and the axial section of the first limiting groove 259, the flexible surgical instrument connection housing 30 is rotated circumferentially until the first projection feature 301 slides out of the circumferential section of the first limiting groove 259, at this time, the second projection feature 302 also slides out of the second limiting groove 261, and each push-pull rod 205 is detached from the side face of the second quick-locking head 254.

Figure 18:
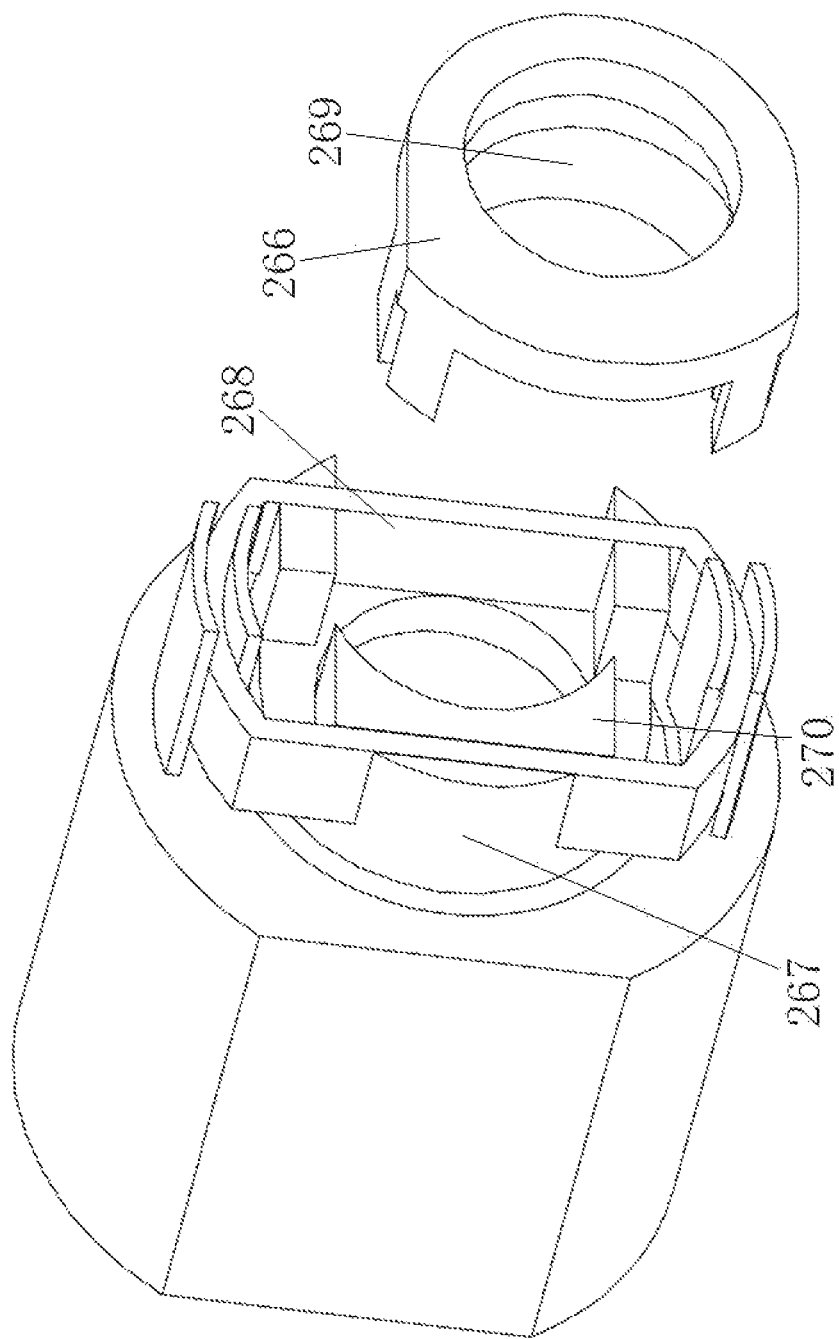
FIG. 18 is an explosive structural schematic diagram of a first locking head of the second type of sterile barrier according to the present invention.
Figure 19:
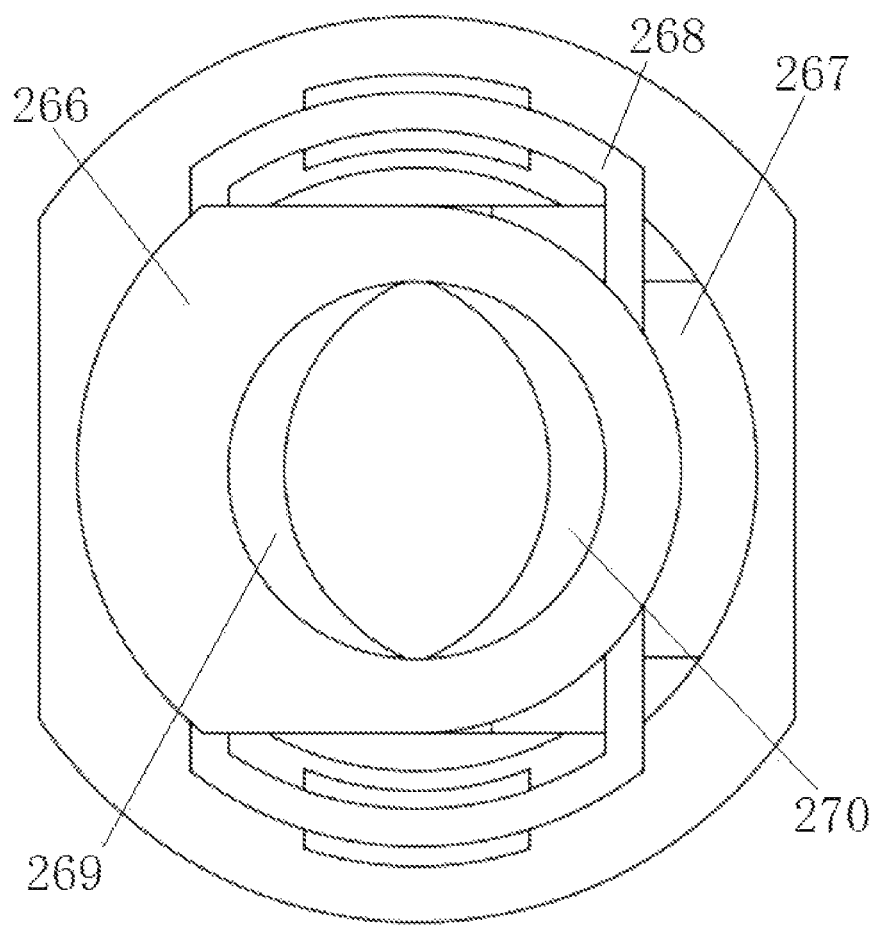
FIG. 19 is a structural schematic diagram of the first locking head of the second type of sterile barrier according to the present invention, viewed from another angle.

As shown in FIGS. 18 and 19, the first quick-locking head 253 comprises two sliders 266, 267 and an elastic ring 268, wherein the two sliders 266, 267 are identical in structure and are engaged together toward each other, and the two sliders 266, 267 hold the elastic ring 268 with straight slots on their respective left and right sides. The two sliders 266, 267 are each provided with a central hole, and the sliders are each provided with a crescent-shaped projection 269, 270 in the respective central hole, the two crescent-shaped projections 269, 270 being arranged oppositely. The locked state of the first quick-locking head 253 of the present invention is as shown in FIG. 19, when the two sliders 266, 267 are subjected to lateral pressure, the elastic ring 268 is deformed, so that the sliders 269, 270 are respectively moved in the direction of the respective forces acting thereon. At this time, the two crescent-shaped projections 269, 270 move away from each other, the centers of the two crescent-shaped projections 269, 270 tend to be coincide, and the formed hole is enlarged. When the two crescent-shaped projections 269, 270 form a closed circular hole, the output rod 222 or the output rod 223 can be inserted into the first quick-locking head 253, and after the pressure is removed, the elastic ring 268 is restored by its own elasticity, thereby pushing the two sliders 266, 267 to move the two crescent-shaped projections 269 and 270 toward each other, and forming a clamping force on the output rod 222 or the output rod 223. An end portion of the output rod 222 or the output rod 223 is provided with an annular groove, and the two crescent-shaped projections 269, 270 are retained in the annular groove of the output rod 222 or the output rod 223, so that the guide rod 252 can be securely connected to the output rod 222 or the output rod 223. Likewise, the output rod 222 or the output rod 223 can be pulled out by exerting lateral pressure on the two sliders 266, 267 again.

In the above embodiment, a surgical end effector 40 (as shown in FIGS. 1 and 2) is provided at the front end of the distal structural body 101, a actuation wire 401 of the surgical end effector 40 passes through the distal structural body 101, the other end thereof is connected to a surgical end effector driving mechanism 402 (as shown in FIG. 6) on the channel fixing plate 120, and the surgical end effector driving mechanism 402 controls the surgical end effector 40 (such as surgical forceps) by physically pushing/pulling the actuation wire 401. The actuation wire 401 may also transfer various forms of energy, such as electrical energy and high-frequency vibrations, to achieve specific surgical functions of the surgical end effector 40. The surgical end effector driving mechanism 402 comprises a first surgical end effector push rod 403 (as shown in FIG. 6) with the front end being securely connected to the actuation wire 401, the rear end of the first surgical end effector push rod 403 is perpendicularly and securely connected to the middle of a second surgical end effector push rod 404, each of two ends of the second surgical end effector push rod 404 is securely connected to one end of a push-pull rod 405, and the other end of the push-pull rod 405 passes through the channel fixing plate 120 and extends rearward. Accordingly, a motor 406 (as shown in FIG. 8) for providing a driving force for the push-pull rod 405 is securely connected to the first fixing plate 208, an output shaft of the motor 406 is connected to one end of a threaded rod 408 via a coupling 407, the other end of the threaded rod 408 is rotatably supported on the fourth fixing plate 213, a nut 409 is connected, in a matching manner, to the threaded rod 408 between the third fixing plate 212 and the fourth fixing plate 213, the nut 409 is securely connected to two rods 410, the front ends of the two rods 410 pass through the fourth fixing plate 213 and jointly support a connection block 411, two output rods 412 spaced apart from each other are securely connected to the front side of the connection block 411, and the output rods 412 and the push-pull rods 405 are also connected via the guide rod 226 on the aforementioned sterile barrier 224.

Figure 20:
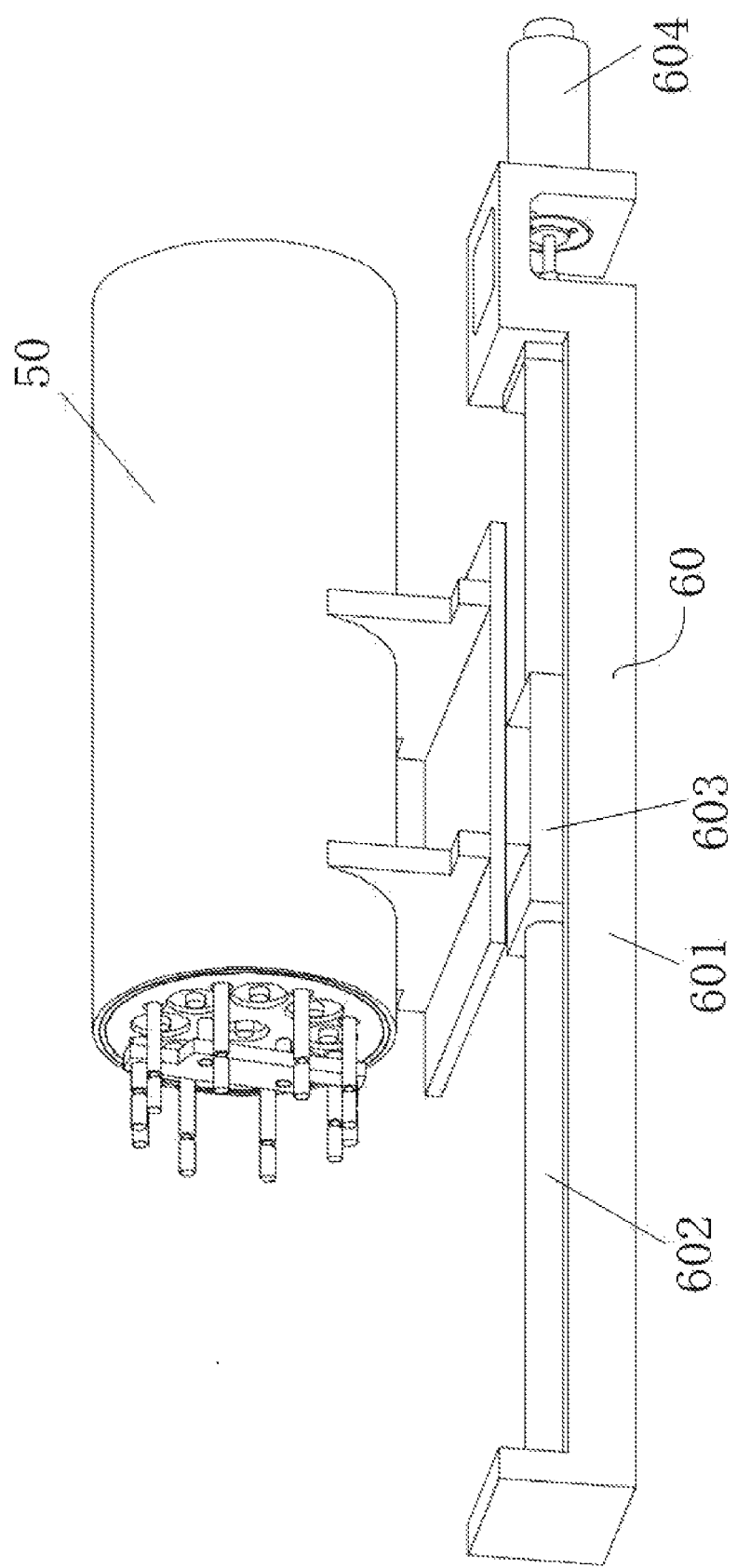
FIG. 20 is a structural schematic diagram of a part of the driving unit and a linear module according to the present invention.

In the above embodiment, as shown in FIGS. 1, 7 and 20, the present invention further comprises a driving unit shell 50, wherein the first fixing plate 208, the second fixing plate 211, the third fixing plate 212 and the fourth fixing plate 213 are all rotatably connected to the driving unit shell 50, an inner wall of the driving unit shell 50 is securely connected to an inner ring gear 501, the first fixing plate 208 is securely connected to a motor 502, an output shaft of the motor 502 is securely connected to a gear 503, and the gear 503 meshes with the inner ring gear 501. When the output shaft of the motor 502 rotates, the gear 503 is driven to rotate, and the gear 503 circumferentially travels along the inner ring gear 501, so as to drive all the structures, other than the motor driving unit shell 50 and the inner ring gear 501, to rotate around an axis of the inner ring gear 501, thereby achieving control over the roll angle of the distal structural body 101 and the surgical end effector 40.

In the above embodiment, as shown in FIGS. 1 and 20, the present invention further comprises a linear module 60, which comprises a bracket body 601 with a sliding groove, a lead screw 602 is rotatably provided on the bracket body 601, the lead screw 602 is sheathed with a slider 603 which is threadedly fitted with the lead screw 602 and is slidably provided in the sliding groove, one end of the bracket body 601 is provided with a motor 604, and an output shaft of the motor 604 is securely connected to the lead screw 602 via a coupling. The driving unit shell 50 is securely connected to the slider 603. When the output shaft of the motor 604 rotates, the slider 603 will drives the driving unit shell 50 to perform linear movement along the sliding groove, so as to implement the feed motion of the flexible surgical instrument 10.

Figure 21:
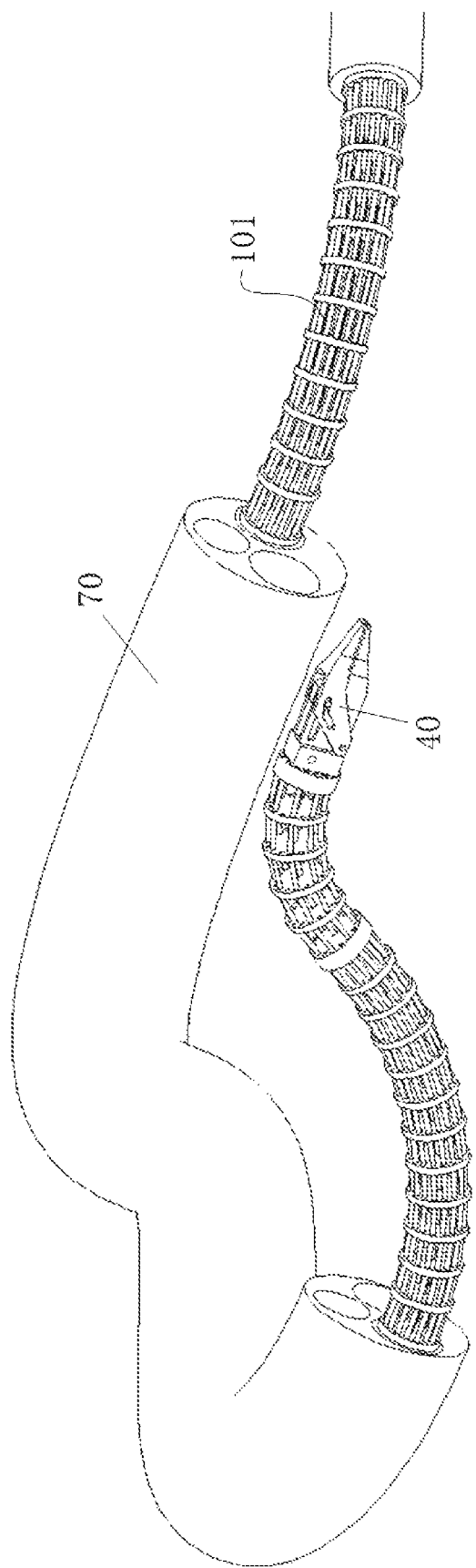
FIG. 21 is a structural schematic diagram of the distal structural body when using a flexible sheath according to the present invention.

In the above embodiment, as shown in FIG. 1, an envelope 122 is provided over the outer side of the distal structural body 101 and functions to improve the smoothness of the distal structural body 101 entering a natural orifice or a surgical incision in the human body. A sheath 70 (as shown in FIG. 2) may also be provided over the outer side of the envelope 122. In an application, the sheath 70 is fixed at a single incision in the abdominal cavity, and the distal structural body 101, together with the envelope 122 and the surgical end effector 40, can freely pass through a through hole in the sheath 70 for the passage of the surgical instrument and have access to the surgical site. As shown in FIG. 21, in another application, the sheath 70 may also be a flexible sheath that can more easily extend into various natural orifices of the human body and adaptively change shape according to the shape of the orifices, one end of the flexible sheath is fixed at the entrance of the orifice, and the distal structural body 101, together with the envelope 122 and the surgical end effector 40, can freely pass through a through hole in the flexible sheath for the passage of the surgical instrument and have access to the surgical site.

The present invention has been illustrated only by the above embodiment, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A flexible surgical instrument system, comprising a flexible surgical instrument and a driving unit, wherein the flexible surgical instrument comprises a flexible continuous body structure composed of a distal structural body, a proximal structural body and a middle connecting body; the distal structural body comprises at least one distal structural segment comprising distal spacing disks, a distal fixing disk, and distal structural backbones; the proximal structural body comprises at least one proximal structural segment comprising proximal spacing disks, a proximal fixing disk and proximal structural backbones; the middle connecting body comprises two channel fixing plates and structural backbone guide channels provided between the two channel fixing plates; the distal structural backbones are securely connected, in one-to-one correspondence to or the same as corresponding proximal structural backbones, a proximal end of each of the proximal structural backbones is securely connected to the proximal fixing disk, the proximal structural backbones passing through the proximal spacing disks, and the structural backbone guide channels, and the distal structural backbones passing through the distal spacing disks, a distal end of each of the distal structural backbones is securely connected to the distal fixing disk; and the driving unit comprises a motor part, a motion conversion part and a plurality of linear motion mechanisms, wherein a sterile barrier is provided between the motion conversion part and the linear motion mechanisms; the motor part comprises a first motor fixing plate and a first motor securely connected to the first motor fixing plate; and the motion conversion part comprises first transmission chains, each of the first transmission chains converts a rotational output of the first motor into a linear motion of two first output rods, the linear motion of corresponding one of the two first output rods is transferred to corresponding one of first push-pull rods at an input end of corresponding one of the plurality of linear motion mechanisms through the sterile barrier, an output end of the corresponding one of the plurality of linear motion mechanisms is securely connected to one end of one driving backbone passing through the proximal spacing disks, and another end of the one driving backbone is securely connected to the proximal fixing disk.

2. The flexible surgical instrument system of claim 1, wherein each of the plurality of linear motion mechanisms comprises a shaft securely connected between the two channel fixing plates, and a slider slidably connected to the shaft, the slider of the corresponding one of the plurality of linear motion mechanisms serves as the output end of the corresponding one of the plurality of linear motion mechanisms and is securely connected to the one driving backbone, the slider of the corresponding one of the plurality of linear motion mechanisms is further securely connected to one end of the corresponding one of first push-pull rods, and another end of the corresponding one of first push-pull rods passes through a proximal channel fixing plate of the two channel fixing plates and is connected to the corresponding one of the two first output rods via the sterile barrier.

3. The flexible surgical instrument system of claim 1, wherein the sterile barrier comprises a guide rod base and a guide rod slidably passing through the guide rod base, a rear end of the guide rod is provided with a first quick-locking head for connection with the corresponding one of the two first output rods, and a front end of the guide rod base is provided with a second quick-locking head for connection with the corresponding one of first push-pull rods; and a sterile membrane for isolating a sterilizable part from an unsterilized part of the flexible surgical instrument system is securely connected to an outer periphery of the sterile barrier.

4. The flexible surgical instrument system of claim 3, wherein the first quick-locking head comprises a screw seat, an insertion hole for having the corresponding one of the two first output rods inserted therein is provided in the screw seat, the screw seat is further provided with a threaded hole in communication with the insertion hole, and a set screw is connected, in a matching manner, to the threaded hole.

5. The flexible surgical instrument system of claim 3, wherein the second quick-locking head comprises two sliders and an elastic ring, the two sliders are engaged together toward each other, the two sliders hold the elastic ring with straight slots on their respective left and right sides, the two sliders are each provided with a central hole, and the two sliders are each provided with a crescent-shaped projection in the respective central hole, the crescent-shaped projection of each of the two sliders being arranged oppositely; and a rear end of the corresponding one of first push-pull rods is provided with a first annular groove.

6. The flexible surgical instrument system of claim 5, wherein a sterile barrier housing is securely connected to an outer periphery of the guide rod base, a quick-locking disk is rotatably connected inside the sterile barrier housing, the quick-locking disk is located in front of the guide rod base, a circumferentially-distributed arc-shaped groove is provided on the quick-locking disk, and a plurality of pairs of semicircular protrusions are arranged on groove walls of the arc-shaped groove; and when the quick-locking disk is rotated, each pair of the semicircular protrusions respectively exerts lateral pressure on the two sliders on the second quick-locking head extending into the first annular groove, to enlarge a projection hole formed by the crescent-shaped projection of each of the two sliders.

7. The flexible surgical instrument system of claim 5, further comprising a flexible surgical instrument connection housing, wherein the proximal structural body and the middle connecting body are both located inside the flexible surgical instrument connection housing; a rear end of the flexible surgical instrument connection housing is provided with a push-pull rod limiting disk, the push-pull rod limiting disk being rotatably connected inside the flexible surgical instrument connection housing, and a plurality of limiting holes are provided in the push-pull rod limiting disk, and each of the plurality of limiting holes is passed by the corresponding one of first push-pull rods, the inner diameter of the plurality of limiting holes being larger than the diameter of the corresponding one of first push-pull rods; and a second annular groove is provided at the same axial position on the corresponding one of first push-pull rods, and the second annular groove is located in front of the first annular groove.

8. The flexible surgical instrument system of claim 1, wherein the sterile barrier comprises a guide rod base and a guide rod slidably passing through the guide rod base; the guide rod is connected between the corresponding one of the two first output rods and the corresponding one of first push-pull rods; and a sterile membrane for isolating a sterilizable part from an unsterilized part of the flexible surgical instrument system is securely connected to the guide rod base.

9. The flexible surgical instrument system of claim 8, wherein a rear end of the guide rod is provided with a first quick-locking head for connection with the corresponding one of the two first output rods, the first quick-locking head comprises two sliders and an elastic ring, the two sliders are engaged together toward each other, the two sliders hold the elastic ring with straight slots on their respective left and right sides, the two sliders are each provided with a central hole, and the two sliders are each provided with a crescent-shaped projection in the respective central hole, the crescent-shaped projection of each of the two sliders being arranged oppositely.

10. The flexible surgical instrument system of claim 8, wherein a front end of the guide rod is provided with a quick-locking head for connection with the corresponding one of first push-pull rods, a rear end of the corresponding one of first push-pull rods is provided with an annular groove, the quick-locking head is provided with a feature groove matching the shape of the rear end of the corresponding one of first push-pull rods, and an opening of the feature groove is located at a side face of the quick-locking head; and
 a flexible surgical instrument connection housing is provided on the outside of the middle connecting body, the middle connecting body and the proximal structural body are both located inside the flexible surgical instrument connection housing, and a front side of the guide rod base is provided with a quick-lock mechanism for connection with the flexible surgical instrument connection housing.

11. The flexible surgical instrument system of claim 10, wherein the quick lock mechanism comprises a circumferential limiting block connected to the guide rod base via a restoring spring, a first limiting groove configured as L-shaped is arranged on an outer side of the circumferential limiting block, a front side edge of the guide rod base is provided with a sterile barrier connection housing, and a front end of the sterile barrier connection housing is provided with a second limiting groove extending circumferentially and having only one opening; a first projection feature configured to slide in the first limiting groove is provided on an inner side of a rear end of the flexible surgical instrument connection housing, and a second projection feature configured to slide in the second limiting groove is provided on an outer side of the rear end of the flexible surgical instrument connection housing; and when the first projection feature slides along a circumferential section of the first limiting groove to a position where an axial section is located, the second projection feature reaches the bottom of the second limiting groove, while the rear end of the corresponding one of first push-pull rods enters into the feature groove of the quick-locking head and forms a matching connection state with the feature groove of the quick-locking head.

12. The flexible surgical instrument system of claim 1, wherein the motion conversion part further comprises a first motion conversion fixing plate, a second motion conversion fixing plate and a third motion conversion fixing plate which are provided in front of the first motor fixing plate;
 each of the first transmission chains comprises a first threaded rod and a second threaded rod which are spaced apart and rotatably supported between the second motion conversion fixing plate and the third motion conversion fixing plate, and a rear end of the first threaded rod passes through the second motion conversion fixing plate and the first motion conversion fixing plate in sequence and is connected to an output shaft of the first motor via a coupling;
 a first gear is securely connected to the first threaded rod between the first motion conversion fixing plate and the second motion conversion fixing plate, the first gear is in transmission connection with a second gear via an idle gear, and
 the second gear is securely connected to the second threaded rod; a first nut and a second nut are respectively connected, in a matching manner, to the first threaded rod and the second threaded rod between the second motion conversion fixing plate and the third motion conversion fixing plate; and
 the two first output rods are respectively securely connected to the first nut and the second nut, and front ends of the two first output rods pass through the third motion conversion fixing plate.

13. The flexible surgical instrument system of claim 12, wherein a spiral direction of the first threaded rod is different from that of the second threaded rod, and the pitch of the first threaded rod is the same as that of the second threaded rod.

14. The flexible surgical instrument system of claim 1, wherein a front end of the distal structural body is provided with a surgical end effector, an actuation wire of the surgical end effector passes through the distal structural body, and another end of the actuation wire is connected to a surgical end effector driving mechanism located between the two channel fixing plates; the surgical end effector driving mechanism comprises a first surgical end effector push rod with a front end being securely connected to the actuation wire, a rear end of the first surgical end effector push rod is perpendicularly and securely connected to the middle of a second surgical end effector push rod, each of two ends of the second surgical end effector push rod is securely connected to one end of each of second push-pull rods, and another end of each of the second push-pull rods passes through a proximal channel fixing plate of the two channel fixing plates and extends rearward; and a second motor is securely connected to the first motor fixing plate, and the motion conversion part further comprises a second transmission chain which converts a rotational output of the second motor into a linear motion of two second output rods; and the linear motion of corresponding one of the two second output rods is transferred to corresponding one of the second push-pull rods via the sterile barrier.

15. The flexible surgical instrument system of claim 12, wherein the motion conversion part further comprises a first motion conversion fixing plate, a second motion conversion fixing plate and a third motion conversion fixing plate which are provided in front of the first motor fixing plate; and the second transmission chain comprises a threaded rod, a rear end of the threaded rod is connected to the second motor via a coupling between the first motor fixing plate and the first motion conversion fixing plate, the second motion conversion fixing plate and the third motion conversion fixing plate jointly and rotatably support the threaded rod, a nut is connected, in a matching manner, to the threaded rod between the second motion conversion fixing plate and the third motion conversion fixing plate, the nut is securely connected to two connecting rods, front ends of the two connecting rods pass through the third motion conversion fixing plate and jointly support a connection block, and the two second output rods are securely connected to a front side of the connection block.

16. The flexible surgical instrument system of claim 1, further comprising a driving unit shell, wherein the first motor fixing plate is rotatably connected to the driving unit shell, an inner wall of the driving unit shell is securely connected with an inner ring gear, the first motor fixing plate is securely connected with a second motor, an output shaft of the second motor is securely connected to a gear, and the gear meshes with the inner ring gear.

17. The flexible surgical instrument system of claim 1, further comprising a driving unit shell and a linear module, wherein the linear module comprises a bracket body, a second motor securely connected to the bracket body, and a linear feed mechanism securely connected to an output shaft of the second motor; an output end of the linear feed mechanism is securely connected to the driving unit shell; and the second motor drives the driving unit shell by means of the linear feed mechanism, to drive the driving unit, the sterile barrier and the flexible surgical instrument to perform a linear motion.

18. The flexible surgical instrument system of claim 17, wherein the linear feed mechanism comprises a lead screw rotatably connected to the bracket body, the lead screw is sheathed with a slider which is threadedly fitted with the lead screw, a linear sliding groove is provided on the bracket body, and the slider is slidably provided in the linear sliding groove; and the output shaft of the second motor is securely connected to the lead screw via a coupling.

19. The flexible surgical instrument system of claim 1, wherein a number of the at least one proximal structural segment is equal to a number of the at least one distal structural segment.

* * * * *